United States Patent
Moehrle et al.

(10) Patent No.: US 10,282,840 B2
(45) Date of Patent: May 7, 2019

(54) IMAGE REPORTING METHOD

(71) Applicants: Armin Moehrle, Chicago, IL (US); Crandon F Clark, Amarillo, TX (US)

(72) Inventors: Armin Moehrle, Chicago, IL (US); Crandon F Clark, Amarillo, TX (US)

(*) Notice: Subject to any disclaimer, the term of this patent is extended or adjusted under 35 U.S.C. 154(b) by 441 days.

(21) Appl. No.: 14/093,470

(22) Filed: Nov. 30, 2013

(65) Prior Publication Data
US 2014/0219500 A1 Aug. 7, 2014

Related U.S. Application Data

(63) Continuation-in-part of application No. 13/188,415, filed on Jul. 21, 2011, now Pat. No. 9,014,485.

(60) Provisional application No. 61/366,492, filed on Jul. 21, 2010.

(51) Int. Cl.
*G06T 7/00* (2017.01)
*G06F 19/00* (2018.01)
*G16H 15/00* (2018.01)
*G16H 50/20* (2018.01)
*G16H 50/70* (2018.01)

(52) U.S. Cl.
CPC .......... *G06T 7/0014* (2013.01); *G06F 19/321* (2013.01); *G16H 15/00* (2018.01); *G06T 2207/10008* (2013.01); *G06T 2207/10081* (2013.01); *G06T 2207/10116* (2013.01); *G06T 2207/30068* (2013.01); *G16H 50/20* (2018.01); *G16H 50/70* (2018.01)

(58) Field of Classification Search
CPC .............................. G06T 7/0081; G06F 19/345
See application file for complete search history.

(56) References Cited

U.S. PATENT DOCUMENTS

| | | |
|---|---|---|
| 6,599,130 B2 | 7/2003 | Moehrle |
| 6,819,785 B1 | 11/2004 | Vining |
| 7,756,317 B2 | 7/2010 | Huo |
| 7,756,727 B1 | 7/2010 | Greenspan |
| 7,773,791 B2 | 8/2010 | Simon |
| 7,844,087 B2 | 11/2010 | Ray |

(Continued)

OTHER PUBLICATIONS

Online Machine Learning, Wikipedia, the free encyclopedia, Feb. 23, 2009, https://en.wikipedia.org/w/index.php?title=Online_machine_learning&direction=prev&oldid=320428309.*

(Continued)

*Primary Examiner* — Vincent Rudolph
*Assistant Examiner* — Raphael Schwartz
(74) *Attorney, Agent, or Firm* — Jonathan D Feuchtwang

(57) ABSTRACT

An image reporting method is provided. The image reporting method comprises the steps of retrieving an image representation of a sample structure from an image source; mapping a generic structure to the sample structure, the generic structure being related to the sample structure; determining a region of interest within the sample structure based on content of the image representation of the sample structure; providing a focused set of representations of diagnostic knowledge which is contextually appropriate to the region of interest and prompting the user to select at least one diagnostic finding from the focused set of knowledge representation or by entering free-form text; and generating a diagnostic report based on the selections and free-form text entries.

25 Claims, 17 Drawing Sheets

(56) References Cited

U.S. PATENT DOCUMENTS

| | | |
|---|---|---|
| 7,916,914 B2 | 3/2011 | Heinlein |
| 7,945,083 B2 | 5/2011 | Zhang |
| 8,150,113 B2 | 4/2012 | Ray |
| 8,150,121 B2 | 4/2012 | Gindele |
| 8,189,886 B2 | 5/2012 | Huo |
| 8,290,227 B2 | 10/2012 | Chen |
| 8,300,908 B2 | 10/2012 | Schneider |
| 8,311,301 B2 | 11/2012 | Gindele |
| 2005/0096530 A1* | 5/2005 | Daw .................. G06F 19/3487 600/408 |
| 2005/0259882 A1* | 11/2005 | Dewaele ....................... 382/243 |
| 2006/0274928 A1* | 12/2006 | Collins et al. ................ 382/132 |
| 2006/0277073 A1 | 12/2006 | Heilbrunn |
| 2007/0274585 A1* | 11/2007 | Zhang et al. ................ 382/132 |
| 2009/0195548 A1 | 8/2009 | Heinlein |
| 2010/0128953 A1* | 5/2010 | Ostrovsky-Berman ....... 382/131 |

OTHER PUBLICATIONS

Rohlfing, Torsten, et al. "Evaluation of atlas selection strategies for atlas-based image segmentation with application to confocal microscopy images of bee brains." NeuroImage 21.4 (2004): 1428-1442.*
Peters, Sebastian, et al.; Visual Representations for Supporting an Ontology-Based Semantic Navigation of Medical Volume Data; Proceedings of the 11th IASTED International Con.

* cited by examiner

EXAM:
MAM BILAT DIGITAL SCREENER W/CAD, 02/15/2007 12:31 PM

CLINICAL INFORMATION:
[Asymptomatic female presents for routine screening mammography,] — 362

COMPARISON:
[None.] [mm/dd/yy]

FINDINGS:
[Two] standard digital views of both breasts were performed and reviewed with the aid of R2 CAD, version 8.3/9.3. The breasts parenchyma is [__]
  - A Subareoiar speculated nodule in the medical aspect of the LCC view at 10 o'clock;
  - A 5mm cluster of micro calcifications in the superior aspect of the RLMO view at 11 o'clock;
  - No suspicious masses, microcalcifications or areas of architectural distortion are present.
— 360

IMPRESSION:
No mammography evidence of malignancy. As long as the patient's physical examination remains normal, routining screening mammogram is recommended annually.

BIRADS:
☐ — 362

RECOMMENDATION:
☐

| Patient List | Interactive | Text |

IHEMammoTest Four-view with CAD(BIRADs 1, Recommendation NS)
2005-12-24 10:20:00

| | | |
|---|---|---|
| 1. Exam | MAM BILAT SCREEN W/CAD, 12/3/2008 9:00 AM | |
| 2. Clinical Info | Asymptomatic female presents for routing screening mammp-graphy. Postive female history of breast cancer in mother at age 47. History of multiple cysts in both breasts. | 362 |
| 3. Comparison | 2/16/2005 and 11/21/2007 | |
| 4. Findings: General | Two standard views of both breasts supplemented with an additional right MLO view with another comparision were performed and reviewed with the aid of R2 CAD, 8.5. The breast parenchyma is heterogeneously dense, unchanged in pattern and distribution. Several partially obscured densities in the right breast are stable dating back to 2005 and are most likely cysts in this patient with a history of previously documentated cysts. No dominant mass, suspisious microcal-cifications or areas of architectural distortion. | 360 |
| 5: Findings: ROI | - a 5mm cluster of micro calcifications in the superior aspect of the RLMO view at 11o'clock | |

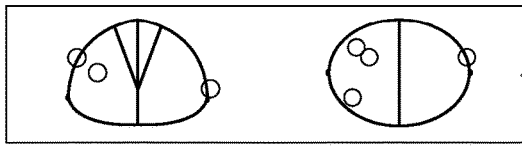

364

| | | |
|---|---|---|
| 6: Impression | No mammographic evidence of malignancy. Given the dense breast parenchyma and age of the patient, digital mammographiy is recommended for future examinations. In patients with dense breast parenchyma, phsical examination is of increased importance as an adjunct to annual mammogra-phy.<br><br>As long as the patient's physical examination remains normal, routine digital screening mammogram is recommended annually. | |
| 7: BIRADS | 2 - Benign finding. | 362 |
| 8: Recommendation | NS - Routine Screening Mammogram. | |

Patient List | Interactive | Text

Jane Smith
BIRADS 2 - Benign Finding
Recommendation: NS - Routine Screening Mammogram      — 364
2005-12-24 10:20:00 cluster of micro calcifications                        cluster of micro calcifications

362

+ Exam                              + Comparison                           362
+ Clinical Info                     − Findings: Lesions                         364
− Findings: General                 Cluster of microcalcifications in left axillary lateral
                                    superior quadrant at 1 o'clock
Two standard views of both breasts supplemented with an
additional right MLO view with another comparision were    − Impression
performed and reviewed with the aid of R2 CAD, 8.5. The
breast parenchyma is heterogeneously dense, unchanged in   No mammographic evidence of malignancy. Given the
pattern and distribution. Several partially obscured densities in   dense breast parenchyma and age of the patient, digital
the right breast are stable dating back to 2005 and are most   mammography is recommended for future examina-
likely cysts in this patient with a history of previously   tions. In patients with dense breast parenchyma, phsical
documented cysts. No dominant mass, suspisious             examination is of increased importance as an adjunct to
microcalcifications or areas of architectural distortion.  annual mammography.

As long as the patient's physical examination remains
                                    normal, routine digital screening mammogram is
                            360     recommended annually.

|                                | prior  | current    | change  |          |
|--------------------------------|--------|------------|---------|----------|
| Volume                         | 3.997  | 3.925 ml   | 0.072 ml| 1.8014 % |
| RECIST diameter                | 20.1   | 19.3 mm    | 0.8 mm  | 3.9801 % |
| max orthogonal diameter        | 19.4   | 18.3 mm    | 1.1 mm  | 5.6701 % |
| WHO area                       | 320.3  | 317.3 mm²  | 3 mm²   | 0.9366 % |
| max 3D diameter                | 21.01  | 20.1 mm    | 0.91 mm | 4.3313 % |
| mean Hounsfield Units          | 41     | 39 HU      | 2 HU    | 4.878 %  |
| standard deviation Hounsfield Units | 19 | 18 HU     | 1 HU    | 5.2632 % |

IMAGE REPORTING METHOD

FIELD OF THE DISCLOSURE

The present disclosure generally relates to image interpretation, and more particularly, to systems and methods for generating image reports.

BACKGROUND OF THE DISCLOSURE

In current image interpretation practice, such as diagnostic radiology, a specialist trained in interpreting images and recognizing abnormalities may look at an image or an image sequence on an image display and report any visual findings by dictating or typing the findings into a report template. The dictating or typing usually includes a narration of the finding, a description about the location of the visual phenomena, abnormality, or region of interest within the images being reported on. The recipient of the report is often left to further analyze the contents of the narrative text report without having easy access to the underlying image. More particularly, in current reporting practice, there is no link between the specific location in the image and the finding associated with the visual phenomena, abnormality, or region of interest, in the image. A specialist also may have to compare a current image with an image and report previously done. This leaves the interpreter to refer back and forth between the image and the report.

Computer-aided detection (CAD) systems are known in the art and are usually confined to detecting and classifying conspicuous structures in the image data. Computer-aided diagnosis (CAD) systems are used in mammography to highlight micro calcification clusters and hyperdense structures in the soft tissue. Computer-aided simple triage (CAST) is another type of CAD, which performs a fully automatic initial interpretation and triage of studies into some meaningful categories (e.g. negative and positive). Unfortunately, these prior art systems are limited to describing the location of the visual phenomena within the image file. By manner of illustration, the coordinate system provided by the CAD system cannot be used to guide a biopsy needle because it fails to identify the relative position within the organ or sample structure.

While such inconveniences may pose a seemingly insignificant risk of error, a typical specialist must interpret a substantial amount of such images in short periods of time, which further compounds the specialist's fatigue and vulnerability to oversights. This is especially critical when the images to be interpreted are medical images of patients with their health being at risk.

General articulation and narration of an image interpretation may be facilitated with reference to structured reporting templates or knowledge representations. One example of a knowledge representation in the form of a semantic network is the Systematized Nomenclature of Medicine-Clinical Terms (SNOMED-CT), which is a systematically organized and computer processable collection of medical terminology covering most areas of clinical information, such as diseases, findings, procedures, microorganisms, pharmaceuticals, and the like. SNOMED-CT provides a consistent way to index, store, retrieve, and aggregate clinical data across various specialties and sites of care. SNOMED-CT also helps in organizing the content of medical records, and in reducing the inconsistencies in the way data is captured, communicated, encoded, and used for clinical care of patients and research.

Another example is the Breast Imaging-Reporting and Data System (BI-RADS), which is a quality assurance tool originally designed for use with mammography. Yet another example is RadLex, a lexicon for uniform indexing and retrieval of radiology information resources, which currently includes more than 30,000 terms. Applications include radiology decision support, reporting tools and search applications for radiology research and education. Reporting templates developed by the Radiological Society of North America (RSNA) Reporting Committee use RadLex terms in their content. Reports using RadLex terms are clearer and more consistent, reducing the potential for error and confusion. RadLex includes other lexicons and semantic networks, such as SNOMED-CT, BI-RADS, as well as any other system or combination of systems developed to help structure and standardize reporting. Richer forms of semantic networks in terms of knowledge representation are ontologies. Ontologies are encoded using ontology languages and commonly include the following components: instances (the basic or "ground level" objects), classes (sets, collections, concepts, classes in programming, types of objects, or kinds of things), attributes (aspects, properties, features, characteristics, or parameters that objects), relations (ways in which classes and individuals can be related to one another), function terms (complex structures formed from certain relations that can be used in place of an individual term in a statement), restrictions (formally stated descriptions of what must be true in order for some assertion to be accepted as input), rules (statements in the form of an if-then sentence that describe the logical inferences that can be drawn from an assertion in a particular form, axioms (assertions, including rules, in a logical form that together comprise the overall theory that the ontology describes in its domain of application), and events (the changing of attributes or relations).

Currently existing image reporting mechanisms do not take full advantage of knowledge representations to assist interpretation while automating reporting. In particular, currently existing systems are not fully integrated with knowledge representations to provide seamless and effortless reference to knowledge representations during articulation of findings. Additionally, in order for such a knowledge representation interface to be effective, there must be a brokering service between the various forms of standards and knowledge representations that constantly evolve. While there is a general lack of such brokering service between the entities of most domains, there is an even greater deficiency in the available means to promote common agreements between terminologies, especially in image reporting applications. Furthermore, due to the lack of more streamlined agreements between knowledge representations in image reporting, currently existing systems also lack means for automatically tracking the development of specific and related cases for inconsistencies or errors so that the knowledge representations may be updated to provide more accurate information in subsequent cases. Such tracking means provide the basis for a probability model for knowledge representations.

In light of the foregoing, there is a need for an improved system and method for generating and managing image reports. There is also a need to automate several of the intermediary steps involved with image reporting and recalling image reports currently existing today. More specifically, there is a need to intertwine automated computer aided image mapping, recognition and reconstruction techniques with automated image reporting techniques. Furthermore, there is a need to integrate image reporting schemes with knowledge representation databases and to provide a means for tracking subsequent and related cases.

SUMMARY OF THE DISCLOSURE

In accordance with one aspect of the disclosure, an image reporting method is provided. The image reporting method comprises the steps of retrieving an image representation of a sample structure from an image source, mapping a generic structure to the sample structure, the generic structure being related to the sample structure and having at least coordinate data defined therein, determining one or more regions of interest within the sample structure based on content of the image representation of the sample structure, automatically associating an annotation to at least one of the regions of interest, and generating a report based at least partially on one of the regions of interest and the annotation.

In a refinement, the generic structure is determined based on a comparison of content of the sample structure to content of a reference structure.

In a related refinement, the image reporting method further includes the steps of displaying a plurality of different views of the same sample structure, and if the region of interest is determined in one of the views, automatically approximating the corresponding spatial locations of the region of interest in the remaining views.

In another refinement, the image reporting method further includes the step of automatically generating a description for the region of interest based on at least one of the annotation and spatial coordinates of the region of interest.

In a related refinement, the description is a location statement describing the spatial coordinates of the region of interest.

In another related refinement, the description is a location statement describing an underlying object within the sample structure that corresponds to the spatial coordinates of the region of interest.

In another related refinement, the description is generated based at least partially on one or more knowledge representation databases.

In yet another related refinement, the descriptions of two or more related reports are tracked for inconsistencies.

In yet another refinement, the step of approximating includes determining a baseline between two shared landmarks of the sample structure in each view, projecting the region of interest onto the baseline to a projection point in a first view, determining a first distance between one of the landmarks and the projection point, determining a second distance between the region of interest to the baseline, determining a band of interest in a second view based on the first distance, determining the corresponding region of interest within the band of interest of the second view, determining a third distance between the corresponding region of interest of the second view and the baseline, and approximating a three-dimensional spatial location of the region of interest based on the first, second and third distances.

In accordance with another aspect of the disclosure, another image reporting method is provided. The image reporting method comprises the steps of retrieving an image representation of a sample structure from an image source, providing a three-dimensional structure that is related to the sample structure, the three-dimensional structure having at least spatial coordinates defined therein, mapping the three-dimensional structure to the sample structure so as to associate regions of the sample structure with the spatial coordinates of the three-dimensional structure, displaying at least one view of the sample structure, determining one or more regions of interest within the sample structure based on content of the image representation of the sample structure, associating an annotation to at least one of the regions of interest, and generating a report based at least partially on one of the regions of interest and the annotation.

In a refinement, the image reporting method further includes the step of automatically generating a description for the region of interest from the annotation and spatial coordinates of the region of interest.

In a related refinement, the description is automatically generated at least partially based on one or more knowledge representation databases.

In accordance with yet another aspect of the disclosure, an image reporting apparatus is provided. The image reporting device includes a user interface providing user access to the image reporting apparatus, the user interface having an input device and an output device, and a computational device in communication with each of the input device, output device and an image source, the computational device having a microprocessor and a memory for storing an algorithm for performing image interpretation and reporting. The algorithm configures the computational device to retrieve an image representation of a sample structure from the image source, provide a generic structure that is related to the sample structure and having at least coordinate data defined therein, map the generic structure to the sample structure such that regions of the sample structure are spatially defined by the coordinate data, display at least one view of the sample structure on the output device, determine a region of interest within the sample structure based on content of the image representation of the sample structure, associate an annotation received from the input device to at least one region of interest, and generate a report based at least partially on the region of interest and the annotation.

In a refinement, the algorithm further configures the computational device to automatically generate a description for the region of interest from the annotation and spatial coordinates of the region of interest.

In a related refinement, the description is automatically generated based at least partially on a dynamic knowledge representation database.

In another related refinement, the description is automatically generated based at least partially on one or more of a Systematized Nomenclature of Medicine-Clinical Terms (SNOMED-CT) database, a Breast Imaging-Reporting and Data System (BI-RADS) database, and a RadLex database.

In another related refinement, the descriptions of two or more related reports are tracked for inconsistencies.

In yet another related refinement, the report is automatically revised based on detected inconsistencies.

These and other aspects of this disclosure will become more readily apparent upon reading the following detailed description when taken in conjunction with the accompanying drawings.

BRIEF DESCRIPTION OF THE DRAWINGS

FIGS. 11A-11C are diagrammatic views of exemplary image reports;

Figure 1:
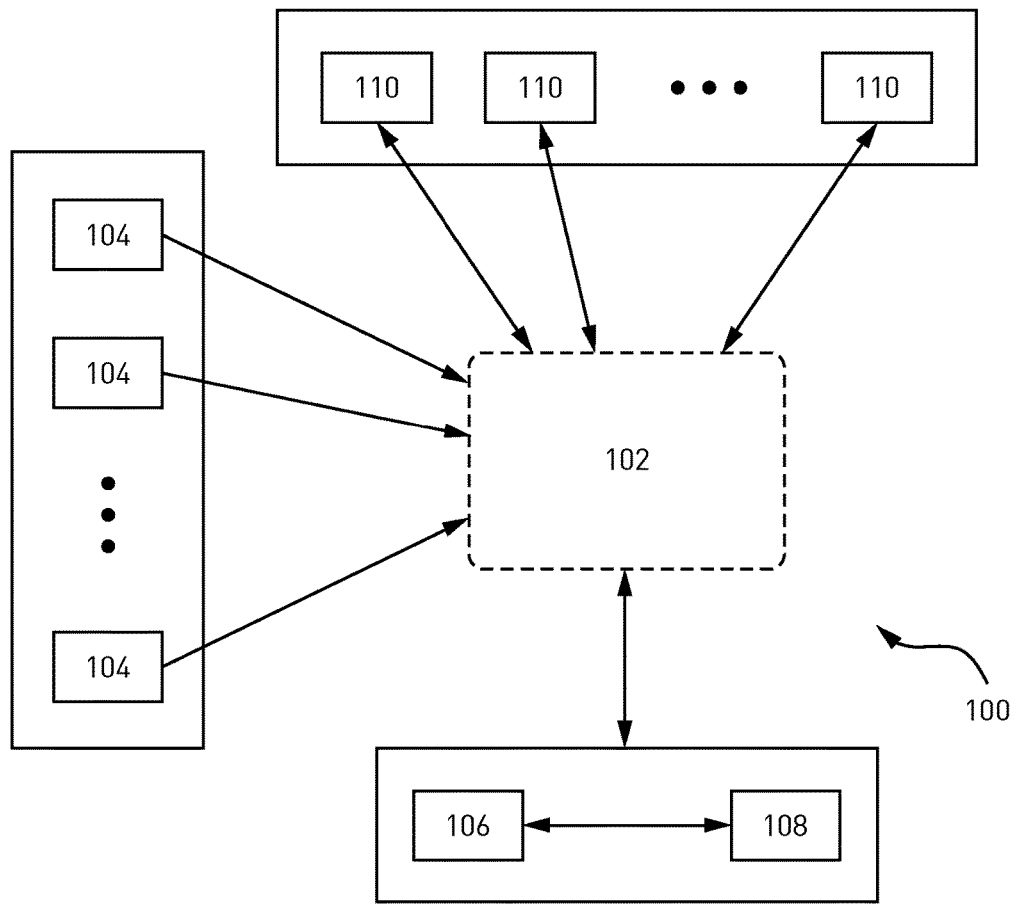
FIG. 1 is a diagrammatic view of an exemplary system for supporting an image reporting method.

While the present disclosure is susceptible to various modifications and alternative constructions, certain illustrative embodiments thereof have been shown in the drawings and will be described below in detail. It should be understood, however, that there is no intention to limit the present invention to the specific forms disclosed, but on the contrary, the intention is to cover all modifications, alternative constructions, and equivalents falling with the spirit and scope of the present invention.

DETAILED DESCRIPTION

Referring now to FIG. 1, an exemplary system 100 within which an image interpretation and reporting method may be integrated is provided. As shown, the system 100 may include a central network 102 by which different components of the system 100 may communicate. For example, the network 102 may take the form of a wired and/or wireless local area network (LAN), a wide area network (WAN), such as the Internet, a wireless local area network (WLAN), a storage or server area network (SAN), and the like. The system 100 may also include image capture devices 104 configured to capture or generate two-dimensional and/or three-dimensional images. In medical imaging, for example, the image capture devices 104 may include one or more of a mammography device, a computed tomography (CT) device, an ultrasound device, an X-ray device, a fluoroscopy device, a film printer, a film digitizer, and the like. One or more images of a sample structure captured by the image capture devices 104 may be transmitted to an image server 106 and/or an image database 108 directly or through a network 102.

The image server 106, image database 108 and/or network 102 of FIG. 1 may be configured to manage the overall storage, retrieval and transfer of images, as in Picture Archiving and Communication System (PACS) in accordance with Digital Imaging and Communications in Medicine (DICOM) standards, for example. In medical applications, each medical image stored in the DICOM database may include, for instance, a header containing relevant information, such as the patient name, the patient identification number, the image type, the scan type, or any other classification type by which the image may be retrieved. Based on the classification type, the server 106 may determine where and how specific images are stored, associate the images with any additional information required for recalling the images, sort the images according to relevant categories and manage user access to those images. In further alternatives, the storage, retrieval and transfer of images may be managed and maintained within the network 102 itself so as to enable services, for example, in an open source platform for individual users from any node with access the network 102. In an application related to medical imaging, for example, each medical image may be tied to a particular patient, physician, symptom, diagnosis, or the like. The stored images may then be selectively recalled or retrieved at a host 110.

As shown in FIG. 1, one or more hosts 110 may be provided within the system 100 and configured to communicate with other nodes of the system 100 via the network 102. Specifically, users with appropriate authorization may connect to the image server 106 and/or image database 108 via the network 102 to access the images stored within the image database 108. In medical applications, for example, a host 110 may be used by a physician, a patient, a radiologist, or any other user granted access thereto. In alternative embodiments, the system 100 may be incorporated into a more localized configuration wherein the host 110 may be in direct communication with one or more image capture devices 104 and/or an image database 108.

Figure 2:
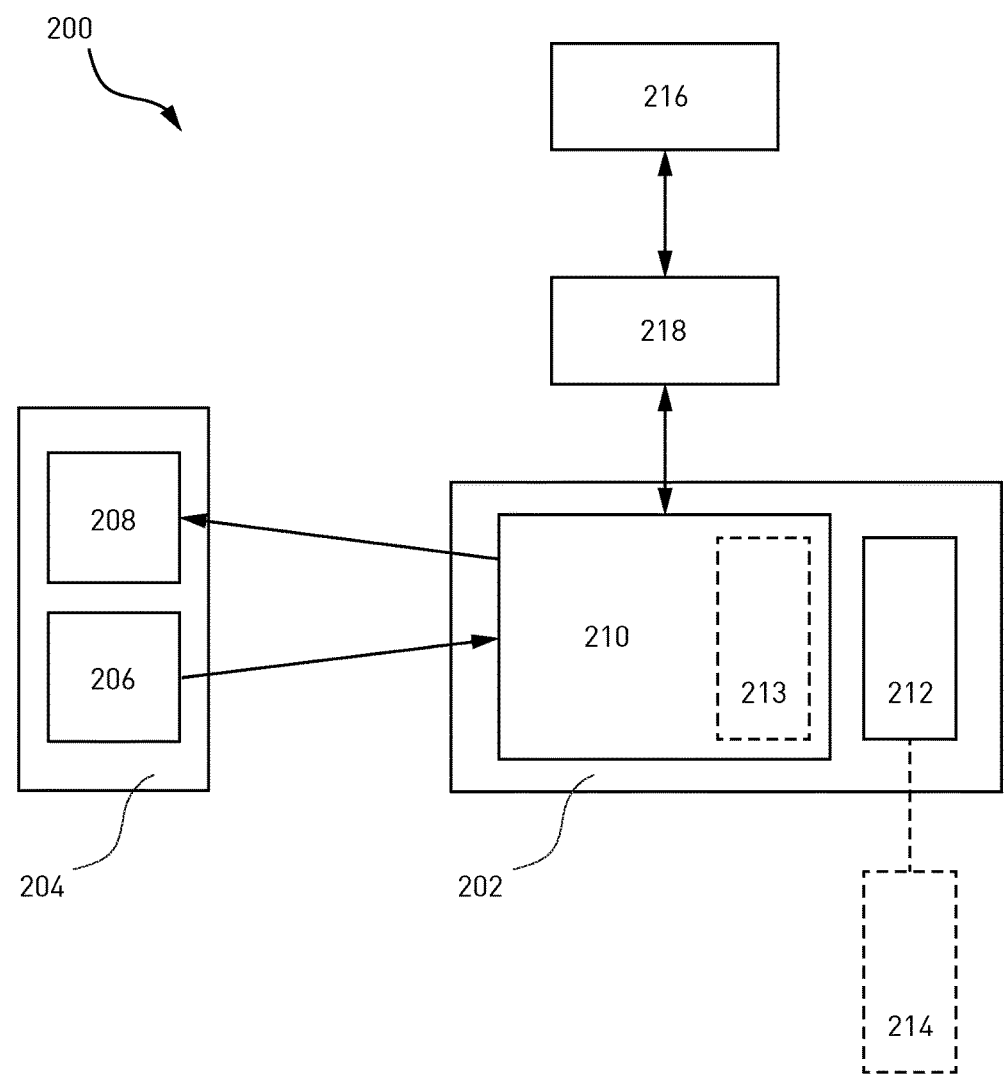
FIG. 2 is a schematic view of an exemplary image reporting device constructed in accordance with the teachings of the disclosure.

Turning now to FIG. 2, one exemplary image reporting device 200 as applied at a host 110 is provided. The image reporting device 200 may essentially include a computational device 202 and a user interface 204 providing user access to the computational device 202. The user interface 204 may include at least one input device 206 which provides, for example, one or more of a keypad, a keyboard, a pointing device, a microphone, a camera, a touch screen, or any other suitable device for receiving user input. The user interface 204 may further include at least one output or viewing device 208, such as a monitor, screen, projector, touch screen, printer, or any other suitable device for outputting information to a user. Each of the input device 206 and the viewing device 208 may be configured to communicate with the computational device 202.

In the particular image reporting device 200 of FIG. 2, the computational device 202 may include at least one controller or microprocessor 210 and a storage device or memory 212 configured to perform image interpretation and/or reporting. More specifically, the memory 212 may be configured to at least one algorithm for performing the image reporting function, while the microprocessor 210 may be configured to execute computations and actions for performing according to the stored algorithm. In alternative embodiments, the microprocessor 210 may include on-board memory 213 similarly capable of storing the algorithm and allowing the microprocessor 210 access thereto. The algorithm may also be provided on a removable computer-readable medium 214 in the form of a computer program product. Specifically, the algorithm may be stored on the removable medium 214 as control logic or a set of program codes which configure the computational device 202 to perform according to the algorithm. The removable medium 214 may be provided as, for example, a compact disc (CD), a floppy, a removable hard drive, a universal serial bus (USB) drive, a flash drive, or any other form of computer-readable removable storage.

Still referring to FIG. 2, the image reporting device 200 may be configured such that the computational device 202 is in communication with at least one image source 216. The image source 216 may include, for example, an image capture device 104 and/or a database of retrievable images, as shown in FIG. 1. In a localized configuration, the computational device 202 may be in direct wired or wireless communication with the image source 216. In still other alternatives, the image source 216 may be established within the memory 212 of the computational device 202. In a network configuration, the computational device 202 may be provided with an optional network or communications device 218 so as to enable a connection to the image source 216 via a network 102.

Figure 3:
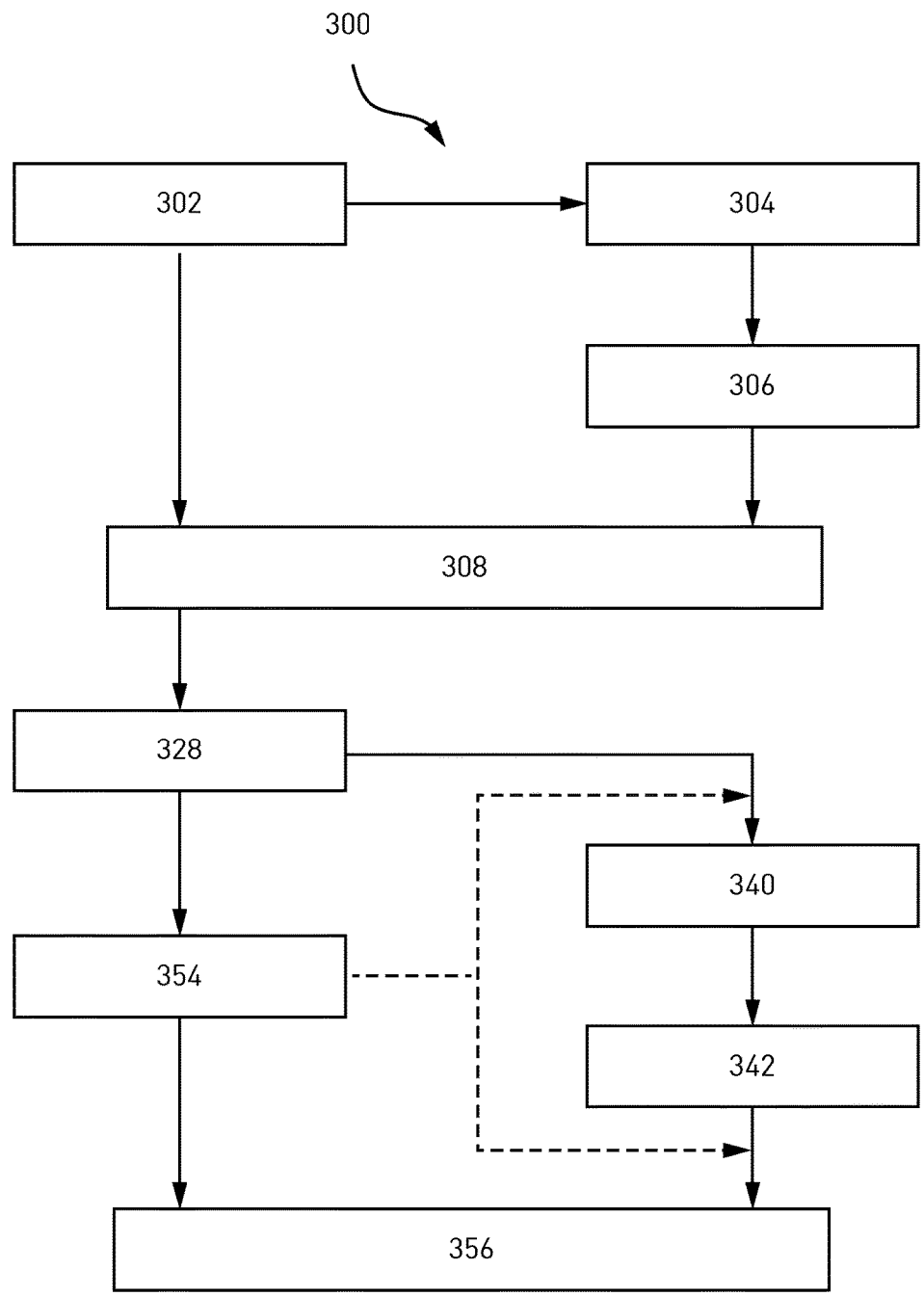
FIG. 3 is a diagrammatic view of an exemplary algorithm for image reporting.

As shown in FIG. 3, a flow diagram of an exemplary algorithm 300 by which an image reporting device 200 may conduct an image reporting session is provided. In an initial step 302, one or more images of a sample structure to be interpreted may be captured and/or recorded. The images may include, for instance, one or more two-dimensional medical images, one or more three-dimensional medical images, or any combination thereof. The sample structure to be interpreted may be, for instance, a patient, a part of the anatomy of a patient, or the like. More specifically, in an image reporting session for medical applications, the images that are captured and/or recorded in step 302 may pertain to a mammography screening, a computer tomography (CT) scan, an ultrasound, an X-ray, a fluoroscopy, or the like.

In an optional step 304, the captured or recorded images may be copied and retrievably stored at an image server 106, an image database 108, a local host 110, or any other suitable image source 216. Each of the copied and stored images may be associated with information linking the images to a sample subject or structure to be interpreted. For instance, medical images of a particular patient may be associated with the patient's identity, medical history, diagnostic information, or any other such relevant information. Such classification of images may allow a user to more easily select and retrieve certain images according to a desired area of interest, as in related step 306. For example, a physician requiring a mammographic image of a patient for the purposes of diagnosing breast cancer may retrieve the images by querying the patient's information via one of the input devices 206. In a related example, a physician conducting a case study of particular areas of the breast may retrieve a plurality of mammographic images belonging to a plurality of patients by querying the image server 106 and/or database 108 for those particular areas.

Upon selecting a particular study in step 306, one or more retrieved images may be displayed at the viewing device 208 of the image reporting device 200 for viewing by the user as in step 308. In alternative embodiments, for example, wherein the image source 216 or capture device 104 is local to the host 110, steps 304 and 306 may be omitted and recorded images may be displayed directly without copying the images to an image database 108.

Figure 4A:
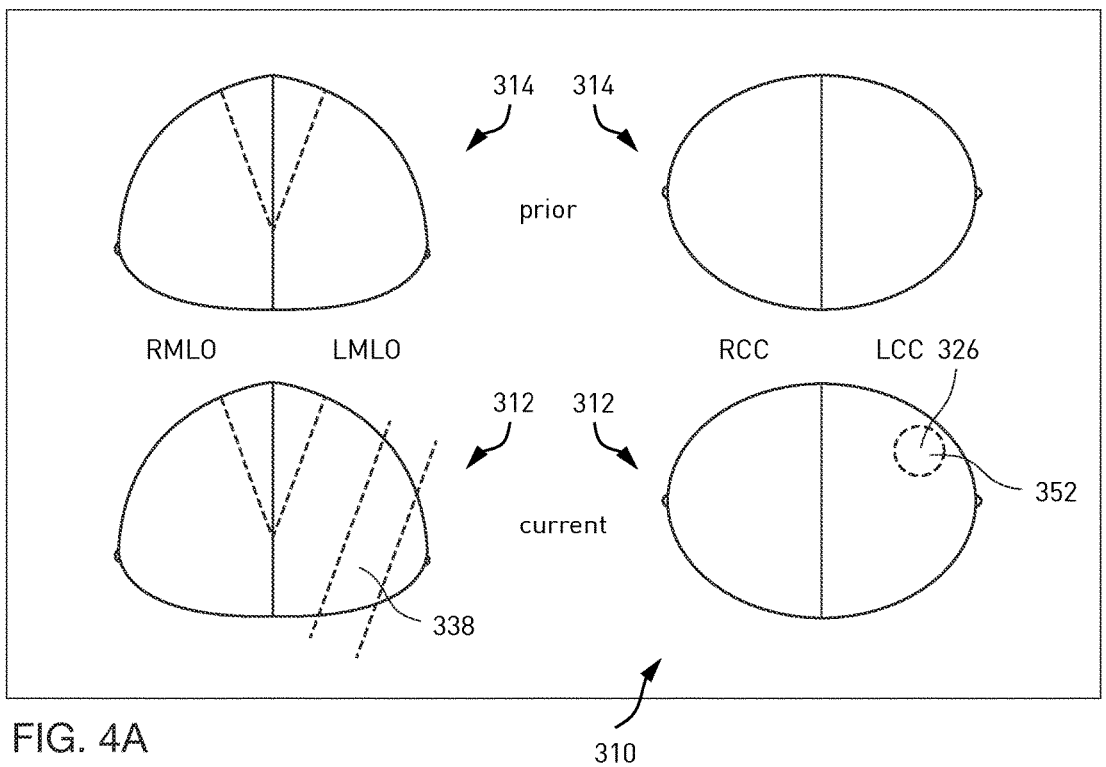
FIGS. 4A-4B are diagrammatic views of a sample structure.
Figure 4B:
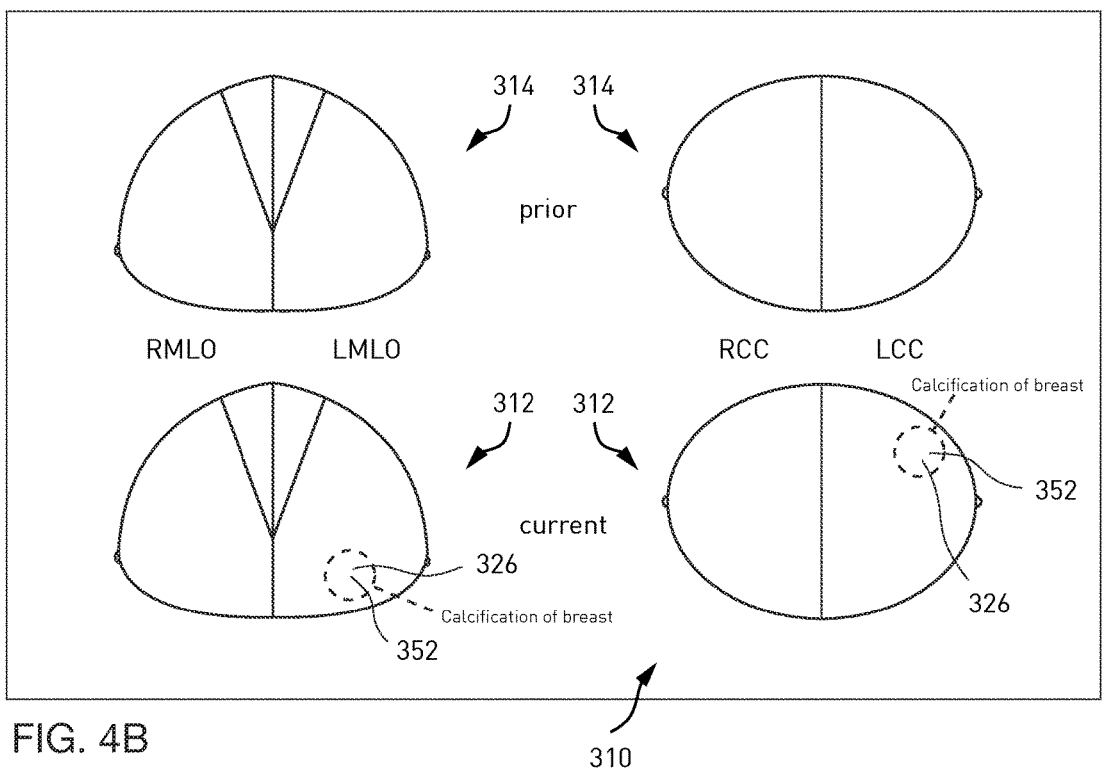

Exemplary images 310 that may be presented at the viewing device 208 are provided in FIGS. 4A-4B. The views contained in each of FIGS. 4A-4B may be simultaneously presented at a single display of a viewing device 208 to the reader so as to facilitate the reader's examination and comprehension of the underlying anatomical object. Alternatively, one or more components or views within each of FIGS. 4A-4B may also be provided as individual views that are simultaneously and/or sequentially presentable at multiple displays of the viewing device 208. The images 310 may include one or more two-dimensional (2D) or three-dimensional (3D) views of an image representation of an image 312 to be interpreted. In the particular views of FIGS. 4A-4B, two-dimensional medical image representations or mammographic images 310 of a breast 312 are provided. Moreover, the displays of FIGS. 4A-4B may include the right mediolateral oblique (RMLO) view of the sample breast 312, as well as the right craniocaudal (RCC) view of the corresponding sample breast 312. Alternatively, one or more three-dimensional views of a sample breast structure 312 may be displayed at the viewing device 208 of the image interpretation and reporting device 200.

Additionally, the images 310 may also provide views of an image representation of a reference structure 314 for comparison. The reference structure 314 may be any one of a prior view of the sample structure 312, a view of a generic structure related to the sample structure 312, a benchmark view of the sample structure 312, or the like. The images 310 may even be provided using different imaging modalities such as computer tomography (CT) scan, an ultrasound, an X-ray, a fluoroscopy, or the like. These different imaging modalities may be linked using image registration techniques commonly known in the art. For the sake of clarity, the term registration as used herein refers to known techniques for correlating a point or a region of interest in a first image with the corresponding location or region in a second image. It should be appreciated that the term registration applies whether images are both from the same imaging modality or if the images were captured using different imaging modalities. Furthermore, the reference structure 314 may be automatically selected and supplied by the image reporting device 200 in response to the sample structure 312 that is retrieved. The image reporting device 200 may prompt the user to confirm that the appropriate reference structure 314 was selected. Moreover, based on certain features of the sample structure 312 in question, the image reporting device 200 may automatically retrieve a comparable reference structure 314 from a collection of reference structures 314 stored at an image source 216, image database 108, or the like. Alternatively, a user may manually select and retrieve a comparable reference structure 314 for viewing.

Figure 5:
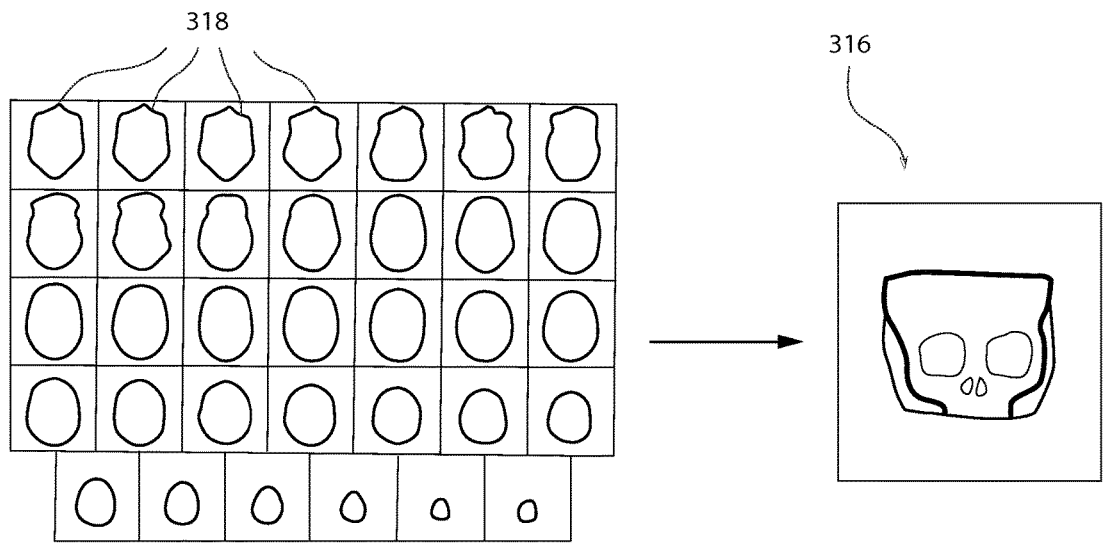
FIG. 5 is a diagrammatic view of a three-dimensional mapping technique.
Figure 6:
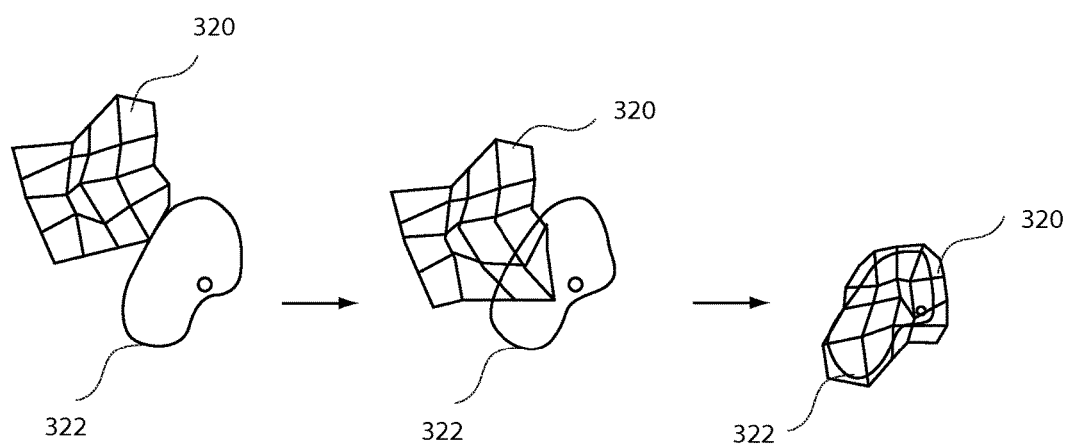
FIG. 6 is a diagrammatic view of a related three-dimensional mapping technique.

Although some retrieved image representations of sample structures 312 may already be in three-dimensional form, many retrieved image representations of a sample structure 312 may only be retrievable in two-dimensional form. Accordingly, the step 308 of displaying an image representation of a sample structure 312 may further perform a mapping sequence so as to reconstruct and display a three-dimensional image representation of the sample structure 312 using any one of a variety of known mapping techniques. As shown in FIG. 5, for example, a computer tomography (CT) image representation of a sample structure 316 of a human head may be retrieved as a collection of two-dimensional images 318, wherein each image 318 may display one lateral cross-sectional view of the sample head structure 316. In such a case, the individual cross-sectional images 318 may be combined to reconstruct the three-dimensional head structure 316 shown. Such mapping techniques may be extended to reconstruct a three-dimensional representation of a complete human anatomy as one sample structure 312. Other known techniques for mapping, as demonstrated in FIG. 6 for example, may exist, wherein a deformable mesh 320 laid over a known data distribution may define the geometric transformation to a three-dimensional structure 322 of unknown data distribution after several iterations of local registrations. Additional mapping techniques may be used in which the deformation of a three-dimensional structure may be represented by a three-dimensional grid, for example, composed of tetraeders, or with three-dimensional radial basis functions. Depending on the resolution applied, the interior content of a three-dimensional image may be well-defined and segmented so as to be automatically discernable by software, for instance. For medical image interpretation practices, such voxel data and the resulting three-dimensional contents may be used to represent and distinguish between any underlying tissues, organs, bones, or the like, of a three-dimensional part of the human anatomy. Still further refinements for mapping may be applied according to, for instance, Hans Lamecker, Thomas Hermann Wenckebach, Hans-Christian Hege. Atlas-based 3D-shape reconstruction from x-ray images. Proc. Int. Conf. of Pattern Recognition (ICPR2006), volume I, p. 371-374, 2006, wherein commonly observed two-dimensional images may be processed and morphed according to a known three-dimensional model thereof so as to reconstruct a refined three-dimensional representation of the image initially observed.

Figure 7A:
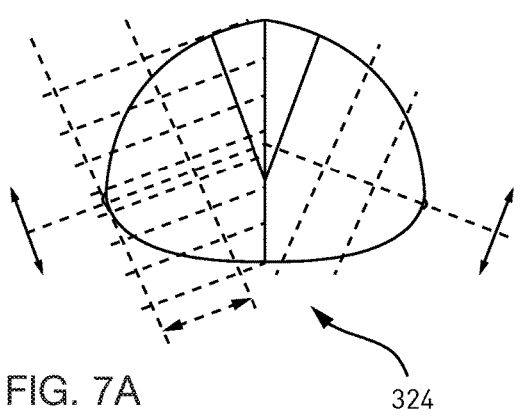
FIGS. 7A-7C are diagrammatic views of a generic structure.
Figure 7B:
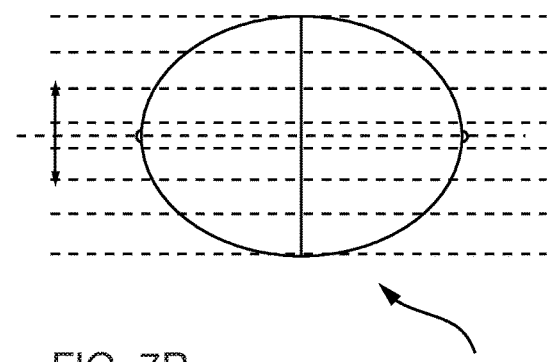
Figure 7C:
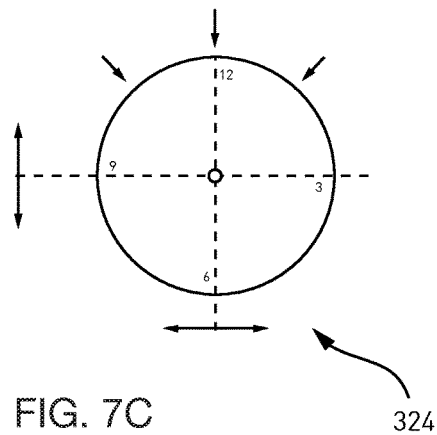
Figure 8A:
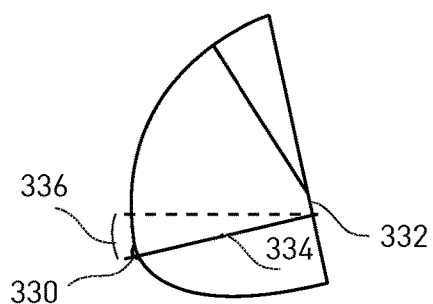
FIGS. 8A-8D are illustrative views of a warping process.
Figure 8C:
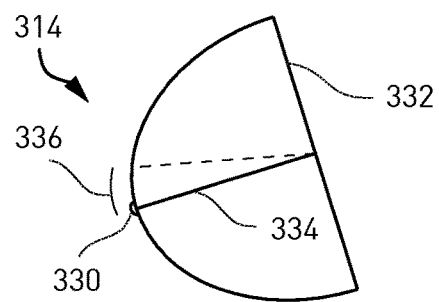
Figure 8B:
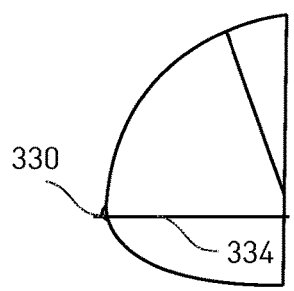
Figure 8D:
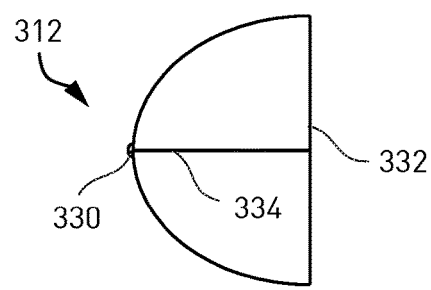

In a similar manner, the algorithm 300 may map a generic structure 324, as shown in FIGS. 7A-7C, to the sample structure 312 of FIGS. 4A-4B. A generic structure 324 may include any known or well-defined structure that is related to the sample structure 312 and/or comparable to the sample structure 312 in terms of size, dimensions, area, volume, weight, density, orientation, or other relevant attributes. Thus the generic structure may be a prior image of the same structure thereby enabling longitudinal comparison of the region of interest. The generic structure 324 may also be associated with known coordinate data. Coordinate data may include pixel data, bitmap data, three dimensional data, voxel data, or any other data type or combinations of data suitable for mapping a known structure onto a sample structure 312. For example, the embodiments of FIGS. 7A-7C illustrate an image representation of a generic breast structure 324 that is comparable in size and orientation to the corresponding sample breast structure 312, and further, includes coordinate data associated therewith. Moreover, in the mammographic images 310 of FIGS. 7A-7C, the coordinate data may be defined according to a coordinate system that is commonly shared by any sample breast structure 312 and sufficient for reconstructing a three-dimensional image, model or structure thereof. By mapping or overlaying the coordinate data of the generic structure 324 onto the sample structure 312, the image reporting algorithm 300 may be enabled to spatially define commonly shared regions within the sample structure 312, and thus, facilitate any further interpretations and/or annotations thereof. By mapping, for instance, the generic breast structure 324 of FIGS. 7A-7C to the sample structure 312 of FIGS. 4A-4B, the algorithm 300 may be able to distinguish, for example, the superior, inferior, posterior, middle, and anterior sections of the sample breast structure 312 as well as the respective clock positions.

As will be described below in further detail, different taxonomies are associated with each generic structure. Thus the selection of a given generic structure restricts the universe of applicable taxonomies. Moreover, different taxonomies are associated with each imaging modality. The taxonomy used to describe a computer tomography (CT) scan of a sample structure is different from the taxonomy used to describe an ultrasound image of the same sample structure. Likewise, X-ray, a fluoroscopy, or the like each use their own unique taxonomy. The image reporting system of the present invention selects the appropriate taxonomy based on the imaging modality and the generic structure thereby facilitating ease of use and ensuring consistent usage of terminology in the reports.

As with reference structures 314, selection of a compatible generic structure 324 may be automated by the image reporting device 200 and/or the algorithm 300 implemented therein. Specifically, an image database 108 may comprise a knowledgebase of previously mapped and stored sample structures 312 of various categories from which a best-fit structure may be designated as the generic structure 324 for a particular study. In one alternative, an approximated generic structure 324 may be constructed based on an average of attributes of all previously mapped and stored sample structures 312 relating to the study in question. Accordingly, the ability of the algorithm 300 to approximate a given sample structure 312 may improve with every successive iteration. Alternatively, a user may manually filter through an image source 216 and/or an image database 108 to retrieve a comparable generic structure 324 for viewing.

Referring back to the algorithm 300 of FIG. 3, once the image representations of the sample structure 312 are mapped and displayed in step 308, the algorithm 300 may enable selection of one or more points or regions of interest (ROIs) within the image representation of the sample structure 312 in step 328. As illustrated in FIGS. 4A-4B, a visual phenomena, abnormality, or region of interest 326 may be determined based on the contents of the image representation of the sample structure 312. For example, in the mammographic images 310 of FIGS. 4A-4B, a region of interest 326 may correspond to a plurality of calcifications disposed within the sample breast structure 312. Such a region of interest 326 may be determined manually by a user viewing the sample structure 312 from an image reporting device 200. One or more regions of interest 326 may also be automatically located by the image reporting algorithm 300. For example, the algorithm 300 may automatically and/or mathematically compare contents of the image representation of the sample structure 312 with the contents of image representation of the reference structure 314, as shown in FIGS. 4A-4B. In some embodiments, the algorithm 300 may similarly enable recognition of contents within an image representation of a generic structure 324.

During such comparisons, it may be beneficial to provide comparison views between a sample structure 312 and a reference structure 314, as demonstrated in FIGS. 4A-4B. However, not all image representations of the reference structure 314 may be retrieved in an orientation that is comparable to that of the sample structure 312, as shown in FIGS. 8A-8D. Accordingly, the algorithm 300 may be configured to automatically warp the position, orientation and/or scale of the image representation of the reference structure 314 to substantially match that of the sample structure 312. In alternative embodiments, the algorithm 300 may be configured to automatically warp the image representation of the sample structure 312 to that of the reference structure 314.

In an exemplary warping process, the algorithm 300 may initially determine two or more landmarks 330, 332 that are commonly shared by the sample and reference structures 312, 314. For example, in the mammographic images 310 of FIGS. 8A-8D, the first landmark 330 may be defined as the nipple of the respective breast structures 312, 314, while the second landmark 332 may be defined as the pectoralis major muscle line. Forming an orthogonal baseline 334 from the first landmark 330 to the second landmark 332 of each structure 312, 314 may provide a basis from which the algorithm 300 may determine the spatial offset that needs to be adjusted. Based on the coordinate mapping performed earlier in step 308 and the detected differences between the respective landmark positions, the algorithm 300 may automatically adjust, rotate, shift, scale or warp one or both of the sample structure 312 and the reference structure 314 to minimize the offset. For instance, in the example of FIGS. 8A-8D, the algorithm 300 may rotate the image representation of the prior reference structure 314 in the direction indicated by arrow 336 until the orientations of the respective landmark baselines 334 are substantially parallel. In an alternative embodiment, the generic structure 314 may be substituted for the reference structure 314, in which case similar warping processes may be employed to minimize any skewing of views.

Still referring to step 328 of FIG. 3, once at least one region of interest 326 has been determined, the algorithm 300 may further link the region of interest 326 with the coordinate data that was mapped to the sample structure 312 during step 308. Such mapping may enable the algorithm 300 to define the spatial location of the region of interest 326 with respect to the generic structure 314 and not only with respect to the view or image representation of the sample structure 312 shown. Moreover, the algorithm 300 may be able to at least partially track the location of the region of interest 326 within the sample structure 312 regardless of the view, position, orientation or scale of the sample structure 312. In particular, if the algorithm 300 is configured to provide multiple views of a sample structure 312, as in the mammographic views of FIGS. 4A-4B for example, step 340 of the algorithm 300 may further provide a range or band of interest 338 in one or more related views corresponding to the region of interest 326 initially established. Based on manual input from a user or automated recognition techniques, step 342 of the algorithm 300 may then determine the corresponding region of interest 326 from within the band of interest 338.

Figures 9A, 9B:
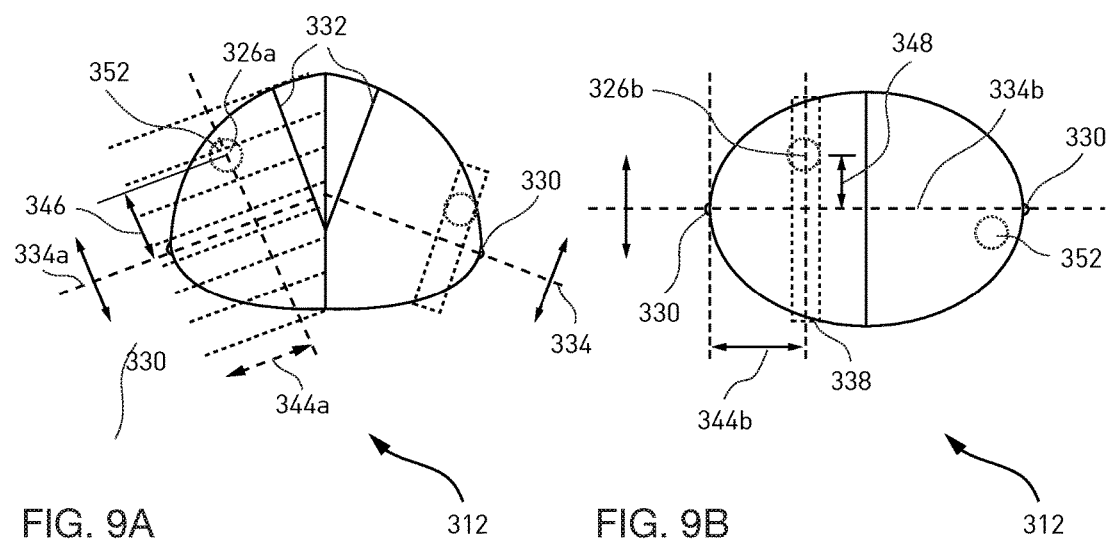
FIGS. 9A-9B are diagrammatic views of another sample structure.

As in the warping techniques previously discussed, in order to perform the tracking steps 340 and 342 of FIG. 3, the algorithm 300 may identify at least two landmarks 330, 332 within the sample structure 312 in question. In the mammographic views of FIGS. 9A-9B shown, for example, the first landmark 330 may be defined as the nipple, and the second landmark 332 may be defined as the pectoralis major muscle line. The algorithm 300 may then define a baseline 334*a* as, for example, an orthogonal line extending from the nipple 330 to the pectoralis major muscle line 332. As demonstrated in FIG. 9A, a user may select the region of interest 326*a* on the right mediolateral oblique (RMLO) view of the sample breast structure 312. After the selection, the algorithm 300 may project the region of interest 326*a* onto the baseline 334*a*, from which the algorithm 300 may then determine a first distance 344*a* and a second distance 346. The first distance 344*a* may be determined by the depth from the first landmark 330 to the point of projection of the region of interest 326*a* on the baseline 334*a*. The second distance 346 may be defined as the projected distance from the region of interest 326*a* to the baseline 334*a*, or a distance above or below the baseline in the mammogram example. Based on the first distance 344*a*, the algorithm 300 may determine a set of corresponding baseline 34*b* and first distance 344*b* in the right craniocaudal (RCC) view of FIG. 9B. Using the baseline 334*b* and first distance 344*b* determined in the second view of FIG. 9*b*, the algorithm 300 may further determine the corresponding band of interest 338 and display the band of interest 338 as shown. From within the band of interest 338 provided, the algorithm 300 may then enable a second selection or determination of the corresponding region of interest 326*b* in the second view. Using the region of interest 326*b* determined in the second view, the algorithm 300 may define a third distance 348 as the distance from the region of interest 326*b* to the baseline 334*b*, or the lateral distance from the nipple 330. Based on the first, second and third distances 344*a-b*, 346, 348, the algorithm 300 may be configured to determine the quadrant or the spatial coordinates of the region of interest 326*a-b*. Notably, while the respective baselines 334*a-b*, and/or the first distances 344*a-b*, of the first and second views of FIGS. 9A and 9B may be comparable in size and configuration, such parameters may be substantially different in other examples. In such cases, warping, or any other suitable process, may be used to reconfigure the respective volumes shown, as well as the respective parameters defined between commonly shared landmarks, to be in a more comparable form between the different views provided.

In a related modification, the algorithm 300 may be configured to superimpose a tracked region of interest 326 to a corresponding location on a reference structure 314 which may be a reference structure, prior sample structure, generic structure 324, or the like. As in previous embodiments, the algorithm 300 may initially determine control points (landmarks) that may be commonly shared by both the sample structure 312 and the reference structure 314. With respect to mammographic images 310, the control points may be defined as the nipple, the center of mass of the breast, the endpoints of the breast contour, or the like. Using such control points and a warping scheme, such as a thin-plate spline (TPS) modeling scheme, or the like, the algorithm 300 may be able to warp or fit the representations of the reference structure 314 to those of the sample structure 312. Once a region of interest 326 is determined and mapped within the sample structure 312, the spatial coordinates of the region of interest 326 may be similarly overlaid or mapped to the warped reference structure 314. Alternatively, a region of interest 326 that is determined within the reference structure 314 may be similarly mapped onto a sample structure 312 that has been warped to fit the reference structure 314.

The aforementioned concept of superimposing a tracked region of interest 326 to a corresponding location on a prior reference structure 314 may be extended to include multiple regions of interest. This enables one to readily determine the longitudinal progression in terms of growth or size and/or number of region(s) of interest over time. Initially there may be only one region of interest which may later grow or shrink. Mapping the initial image on the subsequent image enables accurate tracking of the growth or shrinkage of the region of interest. Additional regions of interest may develop over time and the algorithm 300 enables the user to accurately compare the region of interest longitudinally, i.e., over time. Importantly, the registration process may be automated to facilitate tracking the region of interest over time. However, even with a fully automated registration process it is desirable to prompt the user to manually confirm the registration or mapping of the region of interest and/or identified lesions within the region of interest.

Figures 16, 17:
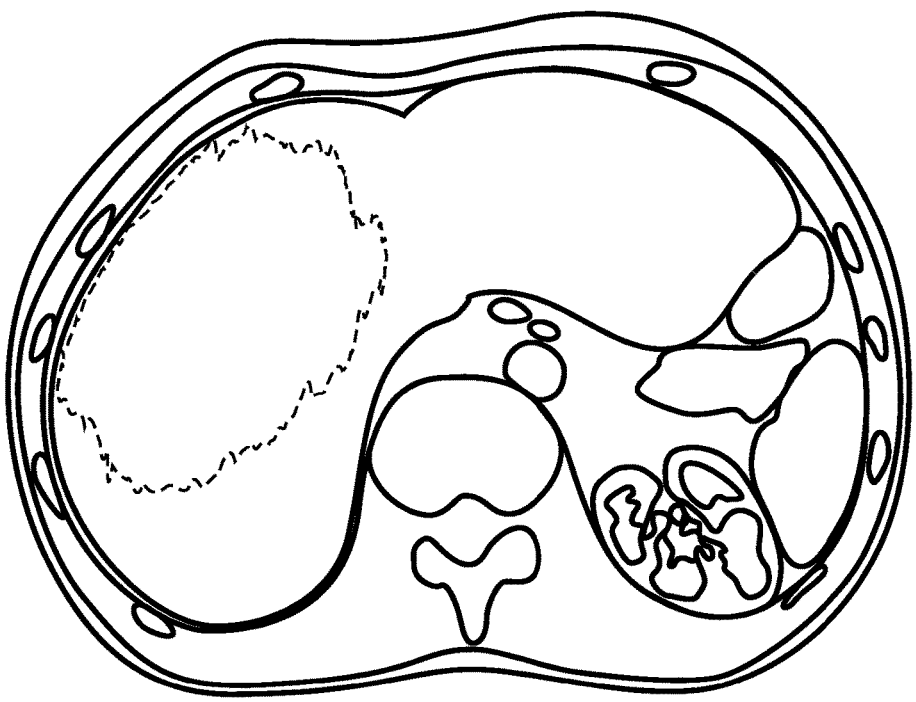
FIG. 16 is a diagrammatic view of a sample structure showing a region of interest.
FIG. 17 is a table providing both current and historical information regarding a region of interest.

FIG. 16 shows a sample structure 312 with the region of interest shown in hashed lines. The user is able to access historical information regarding a region of interest using a pointing device such as a mouse, touch sensitive screen or the like. FIG. 17 is a table which was accessed by the user showing changes in the region of interest. In the example illustrated in FIG. 17 the comparison is made between the current measurements and the previous measurements for the region of interest.

The manual input from the user may consist of simply selecting a region of interest using a pointing device or a touch sensitive screen. In response to the manual input the algorithm 300 may display the outline or contours of a region of interest. In the event that the algorithm 300 cannot detect the outline of the region of interest it may prompt the user to manually trace the outline using a pointing device or the like or the algorithm 300 may simply place a circle or the like around the region of interest. The algorithm 300 uses the outline of the region of interest to automatically compute the size and/or volume of the region.

Alternatively, the algorithm 300 may use automated recognition techniques to identify and display one or more items of interest. The user is then prompted to accept or reject each item of interest.

Regardless of how the item of interest is identified (manual or automated) the user is then prompted to describe the item of interest using the knowledge representation corresponding to the imaging modality and the generic structure. To aid the user and the knowledge representation presented to the user is both organ and modality specific. Thus terms which do not pertain to the imaging modality of the sample are not presented, nor are terms which do not pertain to the organs encompassing the region of interest.

Figure 10A:
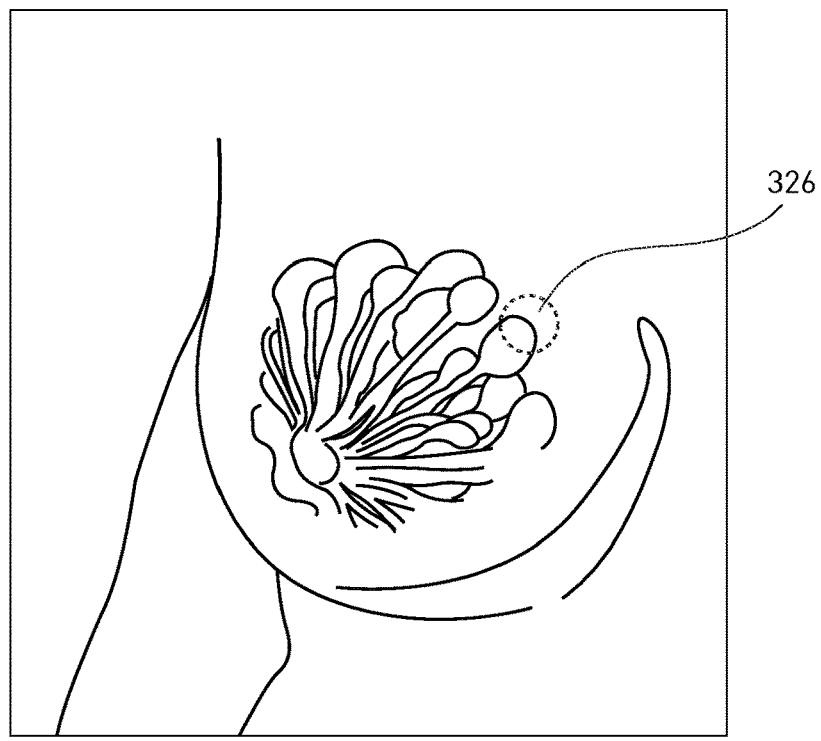
FIGS. 10A-10B are diagrammatic views of yet another sample structure.
Figure 10B:
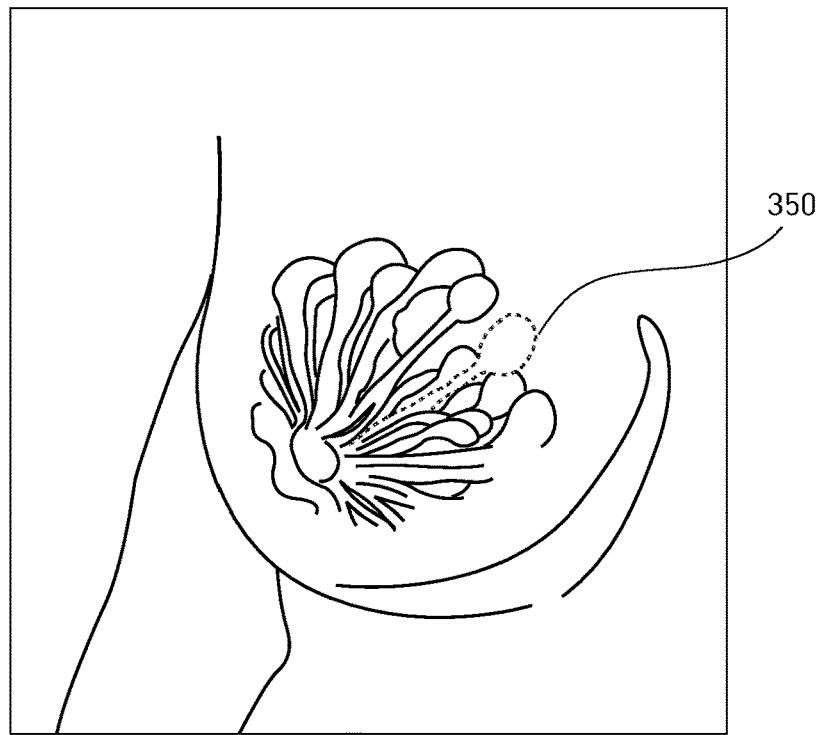

Certain phenomena only occur in certain parts of certain objects such as anatomical organs. The knowledge of where certain phenomena are most likely to occur allows the system to provide a focused set of knowledge representations as a user interface (graphic or audio or both) to an image analyst. This focused knowledge representation allows the analyst to report the findings more efficiently. Focusing the knowledge representation may also be guided by other analytics from other data such as patient history, demographic, geolocation etc. In addition to the structured knowledge representation in form of ontologies, the image analyst might add additional findings in form of free text entry. The image reporting system utilizes natural language analytics in form of statistical semantic analysis of text which is entered as free text and advise on patterns found in the free text. These patterns are basis for the evolution of the ontology. Further extensions of such mapping, marking and tracking may provide more intuitive three-dimensional representations of a sample structure 312, as shown for example in FIGS. 10A-10B. As a result of several iterations of mapping sets and subsets of known coordinate data to a sample structure 312, the algorithm 300 may be able to distinguish the different subcomponents of the sample structure 312 as separable segments, or subsets of data that are grouped according to like characteristics. For instance, in the sample structure 312 of FIGS. 10A-10B, each mammary gland may be defined as one segment 350. Such algorithms 300 may enable a user to navigate through three-dimensional layers of the sample structure 312 and select any point therein as a region of interest 326. In response, the algorithm 300 may determine the subcomponent or segment 350 located nearest to the region of interest 326 indicated by the user and highlight that segment 350 as a whole for further tracking, as shown for example in FIG. 10B.

Once at least one region of interest 326 has been determined and mapped, the algorithm 300 may further enable an annotation 352 of the region of interest 326 in an annotating step 354. For example, a physician viewing the two regions of interest 326 in FIGS. 9A-9B may want to annotate or identify the respective contents of regions of interest 326 as a cluster of microcalcifications and a spiculated nodule. Such annotations 352 may be received at the input device 206 in verbal form by way of a microphone, in typographical form by way of a keyboard, or the like. More specifically, the annotations 352 may be provided in the respective views of the sample structure 312 as plain text, graphics, playback links to audio and/or video clips, or the like. Once entered, each annotation 352 may be spatially associated and tracked with its respective region of interest 326 so as to be accessible and viewable in any related views depicting those regions of interest 326. Data associating each annotation 352 with its respective region of interest 326 may further be retrievably stored with the images 310 via an image server 106 and an image database 108 that is associated with, for example, a Picture Archiving and Communication System (PACS) in accordance with Digital Imaging and Communications in Medicine (DICOM). In an alternative embodiment, the algorithm 300 may be configured to receive an annotation 352 at the first instance of identifying a region of interest 326 and before any tracking of the region of interest 326 is performed to related views. Once the annotation 352 has been associated with the first determination of a region of interest 326, any corresponding regions of interest 326 tracked in subsequent views may automatically be linked with the same initial annotation 352. The algorithm 300 may also allow a user to edit previously established associations or relationships between annotations 352 and their respective regions of interest 326.

Turning back to the algorithm 300 of FIG. 3, step 356 of the algorithm 300 may configure an image reporting device 200 to allow generation of a report based on the mapped regions of interest 326 and accompanying annotations 352. As previously noted, the coordinate data of the generic structure 324 may conform to any common standard (taxonomy) for identifying spatial regions therein. For example, common standards for identifying regions of the breast may be illustrated by the coordinate maps of a generic breast structure in FIGS. 7A-7C. Once a sample structure 312 is mapped with such coordinate data, the algorithm 300 may be able to automatically identify the spatial location of any region of interest 326 or annotation 352 indicated within the sample structure 312. The algorithm 300 may then further expand upon such capabilities by automatically translating the spatial coordinates and/or corresponding volumetric data of the regions of interests 326 and the annotations 352 into character strings or phrases commonly used in a report.

With reference to FIG. 11A, an exemplary report 358 may be automatically provided in response to the regions of interest 326 and annotations 352 of FIGS. 9A-9B. As previously discussed, the mammographic representations of FIGS. 9A-9B depict two regions of interest 326 including a cluster of microcalcifications and a spiculated nodule. According to the coordinate system of FIGS. 7A-7C, the location of the cluster of microcalcifications may correspond to the superior aspect of the RLMO view at 11 o'clock, while the location of the spiculated nodule may correspond to the medial aspect of the LCC view at 10 o'clock. The algorithm 300 may use this information to automatically generate one or more natural language statements or other forms of descriptions indicating the findings to be included into the relevant fields 360 of the report 358, as shown in FIG. 11A. More specifically, the descriptions may include a location statement describing the spatial coordinates of the region of interest 326, a location statement describing the underlying object within the sample structure 312 that corresponds to the spatial coordinates of the region of interest 326, a descriptive statement describing the abnormality discovered within the region of interest 326, or any modification or combination thereof. The algorithm 300 may also provide standard report templates having additional fields 362 that may be automatically filled by the algorithm 300 (which may be manually over-ridden by the user) or manually filled by a user. For example, the fields 362 may be filled with data associated and stored for or with the patient and/or images, such as the exam type, clinical information, and the like, as well as any additional analytical findings, impressions, recommendations, and the like, input by the user while analyzing the images 310.

In further alternatives, the underlying object and/or abnormality may be automatically identified based on a preprogrammed or predetermined association between the spatial coordinates of the region of interest 326 and known characteristics of the sample structure 312 in question. The known characteristics may define the spatial regions and subregions of the sample structure 312, common terms (taxonomy) for identifying or classifying the regions and subregions of the sample structure 312, common abnormalities normally associated with the regions and subregions of the sample structure 312, and the like. Such characteristic information may be retrievably stored in, for example, an image database 108 or an associated network 102. Furthermore, subsequent or newfound characteristics may be stored within the database 108 so as to extend the knowledge of the database 108 and improve the accuracy of the algorithm 300 in identifying the regions, subregions, abnormalities, and the like. Based on such a knowledgebase of information, the algorithm 300 may be extended to automatically generate natural language statements or any other form of descriptions which preliminarily speculate on the type of abnormality that is believed to be in the vicinity of a marked region of interest 326. The algorithm 300 may further be extended to generate descriptions which respond to a user's identification of an abnormality so as to confirm or deny the identification based on the predetermined characteristics. For example, the algorithm 300 may indicate a possible error to the user if, according to its database 108, the abnormality identified by the user is not plausible in the marked region of interest 326. The algorithm 300 may use risk factors contained in the medical record of the patient as part of its decision criteria in indicating possible error or omission or to highlight potential concerns correlated with the risk factors. The user may choose to over-ride the error flag and may optionally provide a reason for over-riding the flag. Alternatively, the user may amend the identification of the abnormality. Thus, if the abnormality identified by the user is not commonly associated with a particular organ or with the patient's risk factors then the potential error will be flagged which may lead the user to revise the patient's risk factors. Moreover, the patient's risk factors indicate a high correlation or predisposition for a particular abnormality which was not identified by the user then the potential error will be flagged which may lead the user to more closely examine the region of interest for any overlooked abnormalities.

One of the aspects of the present invention which should not be overlooked or minimized is the image reporting device and method of the present invention provides an image-based medical record which allows for tracking of diagnosis, decision on treatment and outcomes on a region of interest by region of interest (i.e. lesion by lesion) basis. There are a variety of ways to access the stored information including selecting an (already identified) region of interest by, for example, touching the displayed region with a finger (touch sensitive screen) or using a pointing device. The image reporting device assigns each region of interest a unique label or identifier, and such identifier may also be used to access information pertaining to the diagnosis, treatment, and outcome of treatment. Once the user has selected a given region of interest, he/she is able to select prior annotations, display prior diagnosis, prior decisions on treatment and outcomes of such decisions—all on a region of interest by region of interest basis. Access to prior annotations or the like may be made by, for example, a right mouse click or the like on the region of interest.

Moreover, it should be noted that the image reporting system is intended to be used by both radiologists and oncologists. The radiologist uses the image reporting device 200 to enter diagnostic information and the oncologist uses the image reporting device to enter treatment information as well as treatment outcomes. In this manner the image reporting device facilitates collaboration and efficient sharing of information.

In other alternatives, the algorithm 300 may automatically generate a web-based report 358, as shown in FIGS. 11B-11C for example, that may be transmitted to an image server 106 and/or an image database 108, and viewable via a web browser at a host 110, or the like. As in the report 358 of FIG. 11A, the web-based report 358 may be comprised of initially empty fields 362 which may be automatically filled by the image reporting system 200. The web-based report 358 may alternatively be printed and filled manually by a user. The report 358 may further provide an image representation of the sample structure 312 studied as a preview image 364. The report 358 may additionally offer other view types, as shown for example in FIG. 11C. In contrast to the report 358 of FIG. 11B, the report 358 of FIG. 11C may provide a larger preview image 364 of the sample structure 312 and larger collapsible fields for easier viewing by a user. Providing such a web-based format of the report 358 may enable anyone with authorization to retrieve, view and/or edit the report 358 from any host 110 with access to the image source 216, for example, an image server 106 and an image database 108 of a Picturing Archiving and Communication System (PACS).

Figure 12:
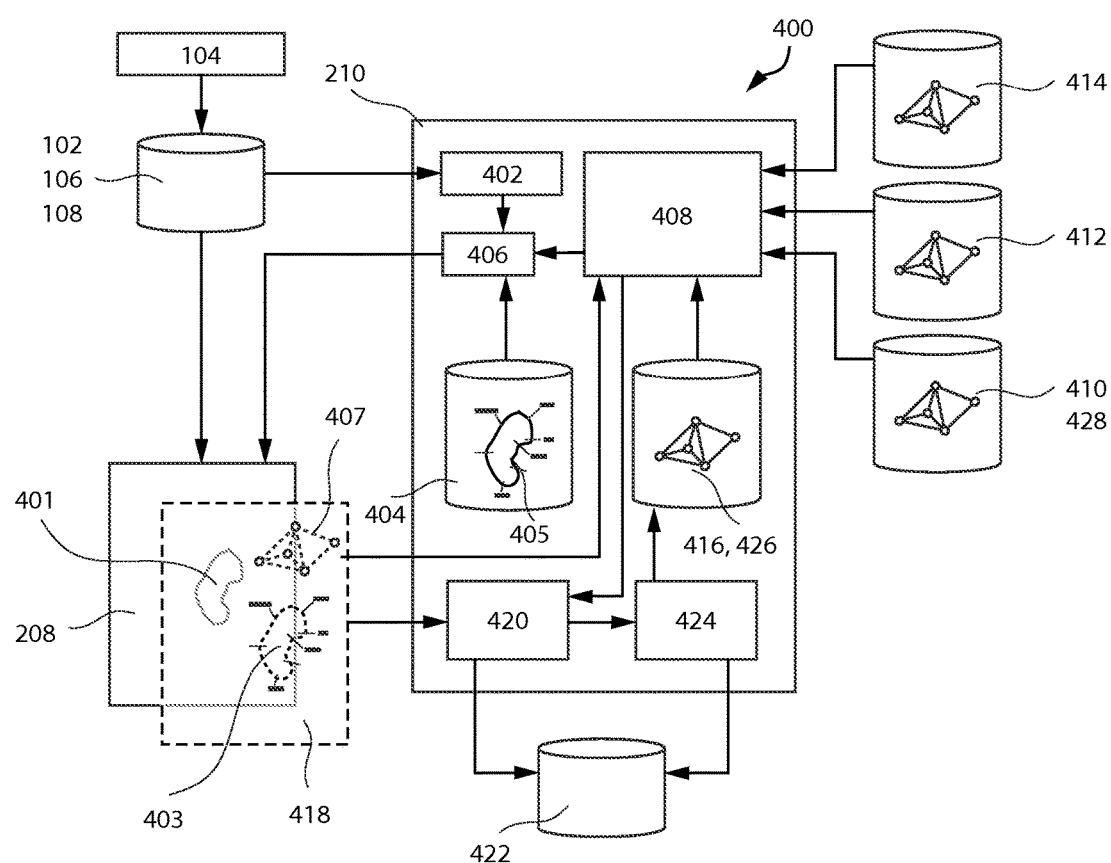
FIG. 12 is a schematic view of an exemplary image reporting system integrated with knowledge representation systems.

In still further modifications, FIG. 12 schematically illustrates an image reporting system 400 that may incorporate aspects of the image reporting device 200, as well as the algorithm 300 associated therewith, and may be provided with additional features including integration with internal and/or external knowledge representation systems. As shown, the image reporting system 400 may be implemented in, for example, the microprocessor 210 and/or memories 212-214 of the image reporting device 200. More specifically, the image reporting system 400 may be implemented as a set of subroutines that is performed concurrently and/or sequentially relative to, for example, one or more steps of the image reporting algorithm 300 of FIG. 3.

An important aspect of the image reporting device 200 is that annotation, procedure history and outcomes are tracked on a lesion by lesion level. Selection of any lesion (by for example, right-clicking on a pointing device such as a mouse or the like) will enable the user to choose to display the previous diagnosis, treatment decisions, and longitudinal progression. In this manner the user is able to see if the treatment regimen has been effective, where the current treatment regimen falls within the internal and/or external knowledge representation systems (ontology). In this manner the user will readily discern whether the current treatment is working and if not will see the next course of action recommended by the knowledge representation systems.

As shown in FIG. 12, once an image 401 of a sample structure that has been captured by an image capture device 104 is forwarded to the appropriate network 102 having an image server 106 and an image database 108, the image 401 may further be forwarded to the microprocessor 210 of the image reporting device 200. In accordance with the image reporting algorithm 300 of FIG. 3, a segmenting subroutine or segmenter 402 of the microprocessor 210 may process the image 401 received into subsets of data or segments 403 that are readily discernable by the algorithm 300. Based on the segmented image 403 of the sample structure and comparisons with a database 404 of generic structures 405, a mapping subroutine or mapper 406 may reconstruct a two- or three-dimensional image representation of the sample structure for display at the viewing device 208. In addition to the image representation, the mapper 406 may also provide a semantic network 407 that may be used to aid in the general articulation of the sample structure, or the findings, diagnoses, natural language statements, annotations, or any other form of description associated therewith. For example, in association with an X-ray of a patient's breast or a mammogram, the semantic network 407 may suggest commonly accepted nomenclature for the different regions of the breast, common findings or disorders in breasts, and the like.

The mapper 406 may also be configured to access more detailed information on the case at hand such that the semantic network 407 reflects knowledge representations that are more specific to the particular patient and the patient's medical history. For example, based on the patient's age, weight, lifestyle, medical history, and any other relevant attribute, the semantic network 407 may be able to advise on the likelihood whether a lesion is benign or requires a recall. Moreover, the semantic network 407 may display or suggest commonly used medical terminologies or knowledge representations that may relate to the particular patient and/or sample structure such that the user may characterize contents of the image representations in a more streamlined fashion.

Still referring to FIG. 12, the mapper 406 may refer to a knowledge representation broker or broker subroutine 408 which may suggest an appropriate set of terminologies (e.g. taxonomy), or knowledge representations (e.g. ontology), based on a structural triangulation or correlation of all of the data available. The broker subroutine 408 may access knowledge representations from external and/or internal knowledge representation databases and provide the right combination of knowledge representations with the right level of abstraction to the reader. More specifically, based on a specific selection, such as an anatomical object, made by the reader, the broker 408 may be configured to determine the combination of knowledge representation databases that is best suited as a reference for the mapper 406 and point the mapper 406 to only those databases. For a selection within a mammography scan, for instance, the broker subroutine 408 may selectively communicate with or refer the mapper 406 to one or more externally maintained sources, such as a Systematized Nomenclature of Medicine-Clinical Terms (SNOMED-CT) database 410, a Breast Imaging-Reporting and Data System (BI-RADS) database 412, a RadLex database 414 of common radiological terms, or any other external database of medical terminologies that may be used for characterizing findings within a sample structure and generating a natural language statement or any other form of description corresponding thereto. The mapper 406 may then refer to those knowledge representation databases in characterizing the selection for the reader using refined knowledge representations. The broker 408 may also be configured to enable the reader to select one or more of the resulting knowledge representations to explore further refinements. The broker 408 may additionally be configured to determine an appropriate level of abstraction of the reader's selection based at least partially on certain contexts that may be relevant to the reader. The contexts may include data pertaining to the patient, the institution to which the reader belongs, the level of expertise of the reader, the anatomical objects in the immediate focus or view of the reader, and the like. The contexts may further include attributes pertaining to different interpretation styles and formats, such as iterative interactive reporting, collective reporting, and the like. Based on such contexts as well as the anatomical object selected by the reader, the image reporting system 400 may be able to provide more refined knowledge representations of the selected object that additionally suit the level of understanding or abstraction of the particular reader. The broker subroutine 408 may similarly access knowledge representations from an internally maintained dynamic knowledge representation database 416. The dynamic knowledge representation database 416 may further provide the broker 408 with the intelligence to provide the right combination of knowledge representations with the right level of abstraction.

Information generated by the mapper 406 may be provided in graphical form and, at least in part, as a transparent layer 418 such that the mapped information may be viewed at the viewing device 208 without obstructing the original image 401 upon which it may be overlaid. A user viewing the information displayed at the viewing device 208 may provide any additional information, such as regions of interest, annotations, statements of findings or diagnoses within the sample structure, and the like. Information input by the user, as well as any other data relevant to the patient, such as the patient's identification, demographic information, medical history, and the like, may be forwarded to a reporting subroutine or report engine 420 for report generation.

The report engine 420 may generate a report, for example, in accordance with the algorithm 300 disclosed in FIG. 3. Furthermore, the report engine 420 may forward the generated report to a medical record database 422 for storage and subsequent use by other care providers attending to the patient. As an additional or optional feature, the report engine 420 of FIG. 12 may be configured to forward a copy of the generated report to a tracking subroutine or case tracker 424. Among other things, the case tracker 424 may serve as a quality tracking mechanism which monitors the amendments or findings in subsequent reports for any significant inconsistencies, such as mischaracterizations, oversights, new findings or diagnoses, disease progression or the like, and responds accordingly by adjusting one or more probability models associated with the particular knowledge representation in question. Probability models may be managed by the dynamic knowledge representation database 416 of the image reporting system 400 and configured to suggest knowledge representations that most suitably represents the anatomical object selected by the reader. Probability models may statistically derive the most appropriate knowledge representation based on prior correlations of data between selected elements or anatomical objects and their corresponding characterizations by physicians, doctors, and the like. Furthermore, the correlations of data and any analytics provided by the probability models may be dynamically updated, validated and invalidated according to any revisions as deemed necessary by the case tracker 424. For example, upon receipt of an alteration of the medical record, which reflects the performance of a treatment, the probability model of the knowledge representation may be validated or altered based on the content of the amendments of the medical record. Based on the tracked results, the case tracker 424 may update the probability model within the dynamic knowledge representation database 416. For instance, a previous data entry of the dynamic knowledge representation database 416 which characterizes a structure with an incorrect statement or finding may be invalidated and replaced with a new data entry which correctly associates the structure with the new amendments or finding. Alternatively, the amendments or finding may be added to the existing statements as an additional finding for a particular combination of information. In such a manner, the case tracker 424 may continuously update and appropriately correct or enrich the representations stored in the dynamic knowledge representation database 416.

The case tracker 424 may use analytics to review free-form (natural language) text entered by the user such as diagnostic finding statements to study patterns of such analysis which may in turn be used to update the focused knowledge representation.

With such access to one or more of a plurality of knowledge databases 410, 412, 414, 416, the image reporting system 400 may be able to determine the best suited natural language statement or description for characterizing elements or findings within a sample structure. Moreover, the image reporting system 400 including at least, for example, a case tracker 424, a dynamic knowledge representation database 416 and a knowledge representation broker 408, may provide a feedback loop through which the image reporting algorithm 300 may generate reports with more streamlined terminologies, automatically expand upon its knowledge representations, as well as adjust for any inconsistencies between related reports and findings.

The medical record 422 may include a variety of patient information. The following list of patient information is intended to be representative but not exhaustive. The medical record may include some or all of the following: data corresponding to physical activities of the patient, patient genetic predisposition including DNA, medical history including prior cancer diagnosis, prior surgery, prior and current drug regimen, blood analysis information including pharmacological (drug absorption data), nutrition and the results of pathology reports. The term risk factors as used herein is intended to refer to one or more items of information from the medical record which either increase or decrease a person's predisposition to certain diseases. Such factors may include age, weight, family history, and the like. The data corresponding to physical activities may be collected using a Nike Fuel Band, Apple iWatch or like data collection devices such as known in the art.

Figure 14:
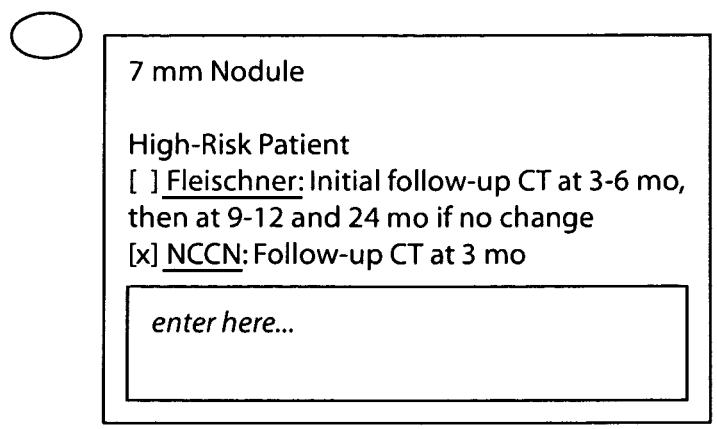
FIG. 14 is a diagrammatic view of showing the user being prompted to select from one of the guidelines or enter a user specified instruction for follow-up care.

Based on the aforementioned characterizing elements or findings within the sample structure the algorithm 300 and/or image reporting system may provide real time decision support by displaying recommendations based on guidelines for management of such findings. For example, in the context of the human lung, the Fleischner Society and the National Comprehensive Cancer Networks (NCCN) each provide guidelines for follow-up and management based on the size of the lesion and the presence of risk factors such as smoking, family history or the like. As shown in FIG. 14 the algorithm 300 prompts the user to select from one of the guidelines or enter a user specified instruction for follow-up care. In the illustration depicted in FIG. 14 the NCCN and Fleishner reflect two different guidelines which the user may select or enter a free-form (natural language) instruction in the box provided. The real time decision support may utilize guidelines found in a local database 426 (FIG. 12) or may access a third-party database 428 over the network.

Figure 15:
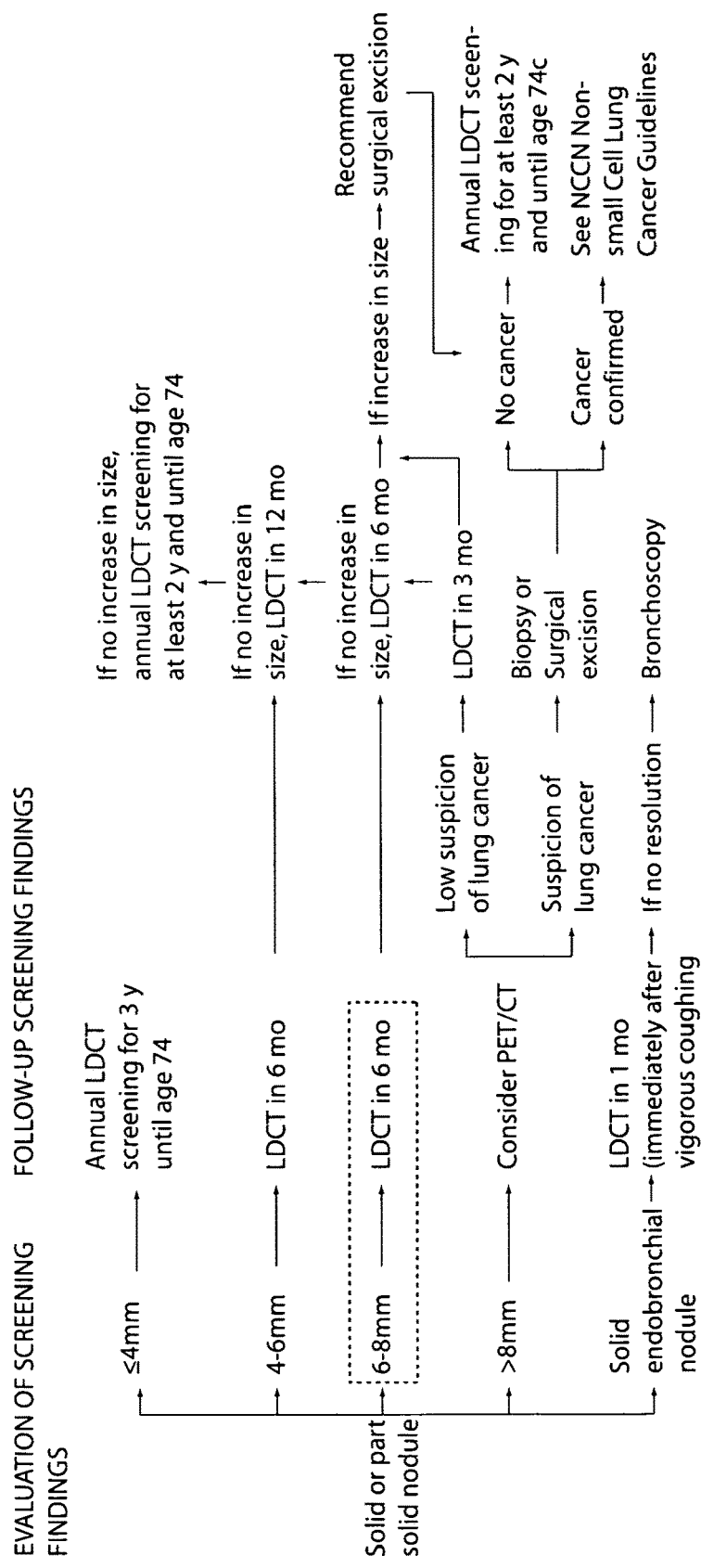
FIG. 15 is a diagrammatic view of a knowledge base or ontology showing recommended treatments for each of a plurality of diagnoses.

In addition to showing the follow-up guidelines recommended by one or more third-party institutions such as Fleischner or NCCN, the algorithm 300 may provide a hyperlink to a knowledge base or the like providing additional insight into the guidelines. See, e.g. FIG. 15. The additional insight may, for example, include showing where the current treatment falls within an overall decision tree.

Figure 13A:
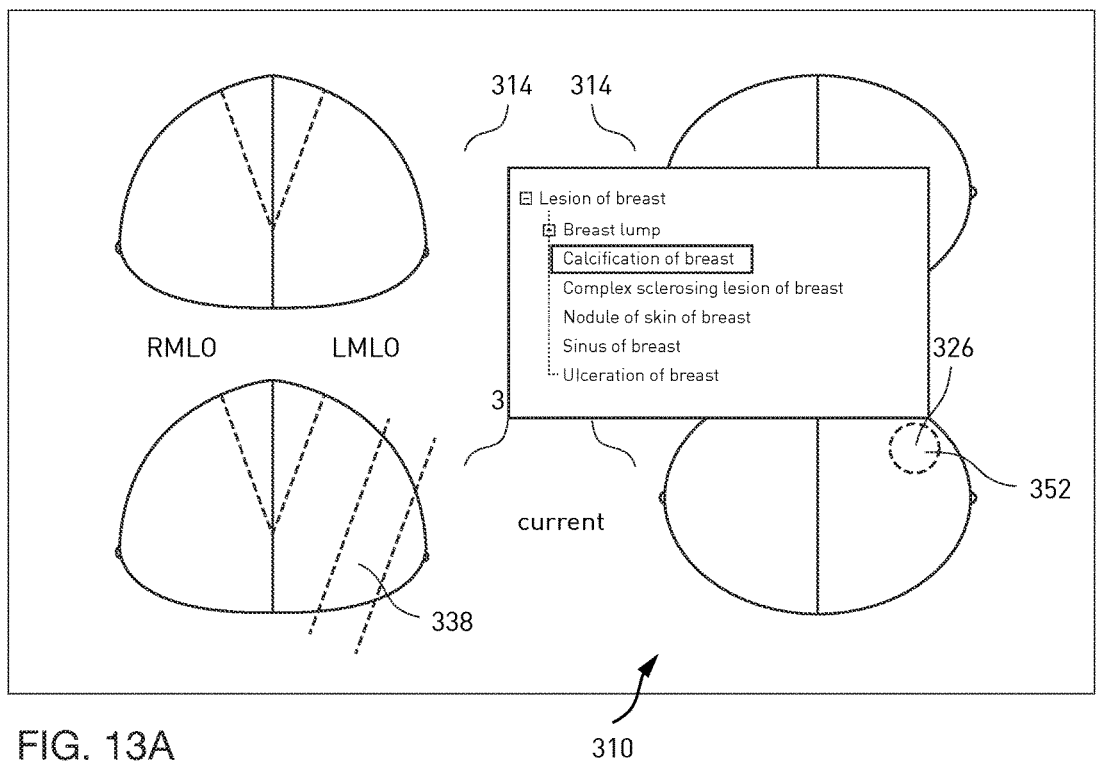
FIGS. 13A and 13B is another diagrammatic view of a sample structure also illustrating knowledge representations.
Figure 13B:
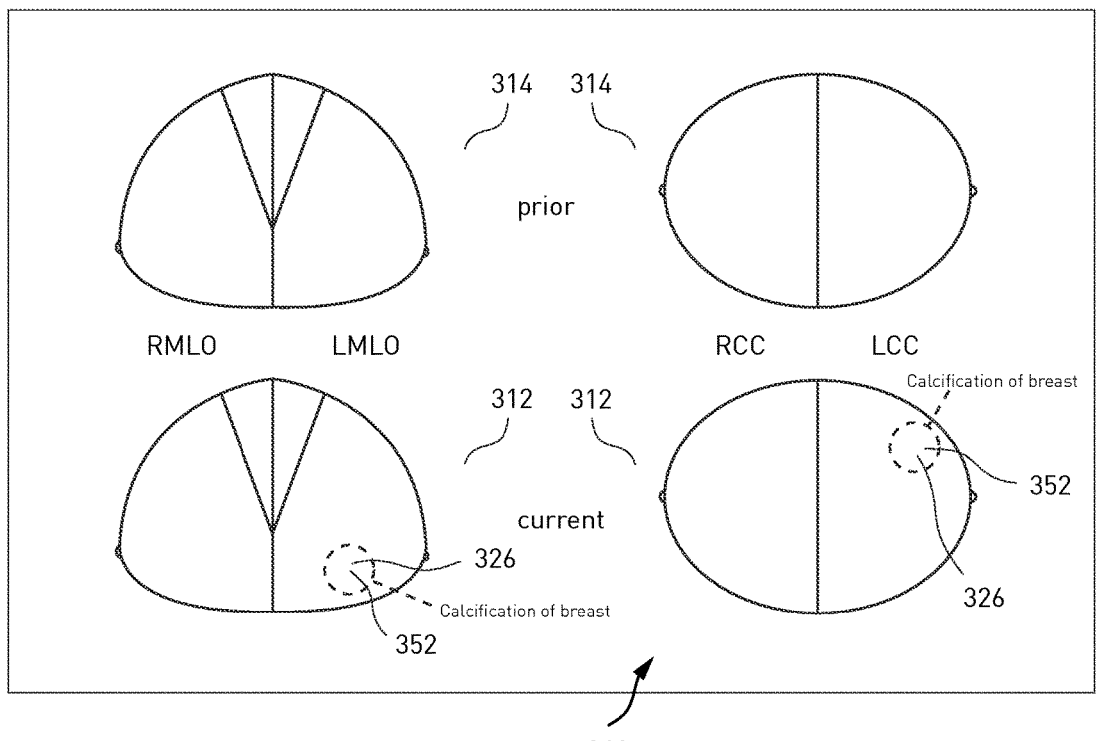

In still further modifications, one or more contents within the transparent layer 418 of the report may be configured to interact with a user through the user interface 204, or the like. For example, the transparent layer 418 may include an interactive knowledge representation displaying semantic relationships between key medical terminologies contained in statements of the report. Using a pointer device, or any other suitable input device 206, a user may select different terms within the report so as to expand upon the selected terms and explore other medical terminologies associated therewith. As the reader interacts with the knowledge representation, the broker might provide a different level of abstraction and a different combination of knowledge representations to assist in hypothesis building and provide information about probability of a malignancy to the reader. A user viewing the report may also make new structural selections from within the image representation of the sample structure displayed. Based on the mapped locations of the user input, such selections made within the transparent layer 418 of the report may be communicated to the knowledge representation broker 408. More particularly, based on the new text selected by the user, the broker subroutine 408 may generate a new semantic network to be displayed within the transparent layer 418 of the report. Based on the new structure or substructure selected by the user, the broker subroutine 408 may determine any new set of medical terminologies, statements, findings, and the like, to include into the report. The broker subroutine 408 may refer to any one or more of the knowledge representation databases 410, 412, 414, 416 shown in FIG. 12 in determining the ontologies and medical terminologies. Any required updates or changes to the report, or at least the transparent layer 418 thereof, may be communicated from the broker subroutine 408 to the report engine 420 such that a new and updated report is automatically generated for immediate viewing. Turning to FIGS. 13A-13B, another exemplary display or user interface that may be provided to the reader at the viewing device 208 is provided. More specifically, the display may follow a format that is similar to the display shown in FIGS. 4A-4B but with the additional feature of providing the reader with knowledge representations, for instance, in accordance with the image reporting system 400 of FIG. 12. As in previous embodiments, a reader may choose to provide an annotation for a selected region of interest 326 by pointing to or indexing the region of interest 326 via the input device 206. In response to the anatomical object underlying or corresponding to the indexed region of interest 326, the image reporting system 400 of FIG. 12 may advise a focused set of knowledge representations most commonly associated with the anatomical object (e.g. an ontology). As shown in FIG. 13A, the knowledge representations may be presented to the reader in the form of a hierarchical menu or diagram showing semantic relationships, or the like. One or more of the knowledge representations displayed may be hierarchically configured and expandable to further reveal specific or more refined knowledge representations. For example, in the embodiment of FIG. 13A, the higher level knowledge representation associated with the selected region of interest 326 may correspond to the lesion of a breast. Expanding upon this knowledge representation may then yield a plurality of common findings within the lesion of the breast. One or more of the resulting findings may also be expanded upon to reveal more refined subcategories, such as breast lumps, calcifications, nodules, sinuses, ulcerations, and the like. From the resulting subcategories, the reader may use the input device 206 to select the most appropriate finding that applies to the patient at hand. Once a knowledge representation is selected, the knowledge representation may be displayed as the annotation associated with the selected region of interest 326, as shown for example in FIG. 13B.

Based on the foregoing, it can be seen that the disclosed method and apparatus provide an improved system and method for generating and managing image reports. The disclosed image reporting device and algorithms serve to automate several of the intermediary steps involved with the processes of generating and recalling image reports today. More specifically, the disclosed method and apparatus serves to integrate automated computer aided image mapping, recognition and reconstruction techniques with automated image reporting techniques. Furthermore, the disclosed method and apparatus aids in streamlining the language commonly used in image reporting as well as providing a means to automatically track subsequent and related cases for inconsistencies.

What is claimed is:

1. An image reporting method, comprising the steps of:
    retrieving an image representation of a sample structure from an image source;
    automatically selecting a generic structure from among a plurality of generic structures based on a comparison of content and imaging modality of the sample structure to content and imaging modality of the generic structure, the selected generic structure being related to the sample structure by both imaging modality and one or more attributes selected from the group (size, dimensions, area, shape, volume, weight, density, location, anatomical organ, and orientation), at least one knowledge representation associated with said selected generic structure, the knowledge representation being specific to the anatomical organ and the imaging modality;
    mapping the selected generic structure to the sample structure, the selected generic structure having coordinate data defined therein;
    automatically determining at least one region of interest within the sample structure or prompting the user to select a region of interest;
    automatically linking the at least one region of interest with the mapped coordinate data;
    automatically generating natural language statements describing a location in an anatomy of the at least one region of interest using the coordinate data;
    for each position on the anatomical organ, automatically providing a focused set of representations of diagnostic knowledge, and prompting the user to select at least one diagnostic finding from the focused set of knowledge representation or by entering free-form text;
    automatically generating a diagnostic report based on the selections or free-form text entries, and including the natural language statements describing the location in the anatomy of the region of interest; and
    retrievably storing the diagnostic report in an electronic medical record;
    wherein said free-form text entries are used to update the knowledge representation.

2. The method of claim 1 further comprising the step of retrieving information regarding risk factors from an electronic medical record, wherein the step of providing a focused knowledge representation is based on the at least one region of interest and risk factors.

3. The method of claim 2, retrieving information regarding genetic predisposition from the electronic medical record, wherein the step of providing a focused knowledge representation is based on the at least one knowledge representation associated with said selected generic structure, the at least one region of interest, risk factors, imaging modality and genetic predisposition.

4. The method of claim 2, wherein the step of providing a focused knowledge representation includes accessing guidelines from a third-party database.

5. The method of claim 1, wherein the user is prompted to accept the automatically mapped generic structure or select an alternate generic structure.

6. The method of claim 1, wherein the step of determining the at least one region of interest within the sample structure is performed automatically based on pre-defined criteria.

7. The method of claim 6, wherein the pre-defined criteria correspond to the generic structure.

8. The method of claim 1, wherein the step of determining the at least one region of interest within the sample structure includes a sub-step of automatically identifying the at least one region of interest in the sample structure using criteria corresponding to the generic structure, and a sub-step of prompting a user to accept or reject the identified at least one region of interest.

9. The method of claim 1, wherein the step of automatically warping includes:
    determining a set of shared control points in each of the sample structure and the generic structure views;
    warping the generic structure view based on the control points to approximate the sample structure view; and
    determining corresponding spatial coordinates of the at least one region of interest in the generic structure view.

10. The method of claim 1, wherein the reference structure is a prior image representation of the sample structure.

11. The method of claim 1, wherein the reference structure is an image representation of the generic structure.

12. The method of claim 1 further comprising the step of retrievably storing one or more of the mapped sample structure, at least one region of interest, diagnosis, a selected treatment and an outcome of treatment in a database.

13. The method of claim 12, wherein the diagnosis, selected treatment and outcome of treatment is provided to a user for each said at least one region of interest.

14. The method of claim 1, wherein the step of providing a focused knowledge representation includes a sub-step of displaying a knowledgebase of diagnosis options applicable to the at least one region of interest and prompting the user to select one or more of the diagnosis options or enter a free-form natural-language treatment option.

15. The method of claim 14, wherein diagnosis options which have a positive correlation to risk factors contained in an electronic medical record are either pre-selected or visually emphasized to the user.

16. The method of claim 1, wherein the step of providing a focused knowledge representation includes a sub-step of prompting a user to select a knowledgebase from among a list of at least two knowledgebases, displaying the selected knowledgebase of diagnosis options, and prompting the user to select one or more of the diagnosis or enter a free-form natural language diagnosis.

17. The method of claim 1, wherein the diagnostic report is added to the electronic medical record.

18. The method of claim 1, wherein the at least one region of interest delineates the boundary of a visual phenomena or abnormality.

19. The method of claim 1, wherein the mapped generic structure includes coordinate data defined therein; and further comprising the step of automatically linking the at least one region of interest with the coordinate data, thereby providing a spatial location of the at least one region of interest with respect to the sample structure.

20. An image reporting method, comprising the steps of:
retrieving an image representation of a sample structure from an image source;
automatically selecting a generic structure among a plurality of generic structures based on a comparison of content and imaging modality of the sample structure to content and imaging modality of the generic structure, the selected generic structure having coordinate data defined, the selected generic structure being related to the sample structure by both imaging modality and one or more attributes selected from the group of (size, dimensions, area, shape, volume, weight, density, location, anatomical organ, and orientation), at least one knowledge representation associated with said generic structure, the at least one knowledge representation being specific to the anatomical organ of the generic structure and an imaging modality used to capture the generic structure;
mapping the selected generic structure to the sample structure;
automatically determining at least one region of interest within the sample structure or prompting the user to select a region of interest;
linking the at least one region of interest with the coordinate data, thereby providing a spatial location of the at least one region of interest with respect to the sample structure;
for each position on the anatomical organ providing a focused set of representations of diagnostic knowledge and prompting the user to select at least one diagnostic finding from the focused set of knowledge representation or by entering free-form text; and
automatically generating a diagnostic report based on the selections, spatial location of the at least one region of interest, and free-form text entries;
wherein a quality tracking routine uses analytics to review the free-form text entered by the user to study patterns and updates the knowledge representation.

21. The method of claim 1 wherein in response to selection of a give said at least one region of interest, prompting a user to choose which information to display from the group (diagnosis, treatment decisions, and longitudinal progression).

22. An image reporting method, comprising the steps of:
retrieving an image representation of a sample structure from an image source;
automatically selecting a generic structure from among a plurality of generic structures based on a comparison of content and imaging modality of the sample structure to content and imaging modality of the generic structure, the selected generic structure being related to the sample structure by both imaging modality and one or more attributes selected from the group (size, dimensions, area, shape, volume, weight, density, location, anatomical organ, and orientation), at least one knowledge representation associated with said selected generic structure, the knowledge representation being specific to the anatomical organ and the imaging modality;
mapping the selected generic structure to the sample structure, the selected generic structure having coordinate data defined therein;
automatically determining at least one region of interest within the sample structure or prompting the user to select a region of interest;
automatically linking the at least one region of interest with the mapped coordinate data;
automatically generating natural language statements describing a location in an anatomy of the at least one region of interest using the coordinate data;
for each position on the anatomical organ, automatically providing a focused set of representations of diagnostic knowledge, and prompting the user to select at least one diagnostic finding from the focused set of knowledge representation or to enter free-form text;
automatically generating a diagnostic report based on the selections and free-form text entries, and including the natural language statements describing the location in the anatomy of the region of interest; and
retrievably storing the diagnostic report in an electronic medical record;
wherein a quality tracking routine retrieves one or more diagnostic reports for the at least one region of interest which were previously generated, compares the results of the each of the one or more diagnostic reports to identify a pattern of mischaracterizations, and adjusts the knowledge representation.

23. An image reporting method, comprising the steps of:
retrieving an image representation of a sample structure from an image source;
automatically selecting a generic structure from among a plurality of generic structures based on a comparison of content and imaging modality of the sample structure to content and imaging modality of the generic structure, the selected generic structure being related to the sample structure by both imaging modality and one or more attributes selected from the group (size, dimensions, area, shape, volume, weight, density, location, anatomical organ, and orientation), at least one knowledge representation associated with said selected generic structure, the knowledge representation being specific to the anatomical organ and the imaging modality;
mapping the selected generic structure to the sample structure, the selected generic structure having coordinate data defined therein;
automatically determining at least one region of interest within the sample structure or prompting the user to select a region of interest;
automatically linking the at least one region of interest with the mapped coordinate data;
automatically generating natural language statements describing a location in an anatomy of the at least one region of interest using the coordinate data;
for each position on the anatomical organ, automatically providing a focused set of representations of diagnostic knowledge corresponding to the position on the anatomical organ, and prompting the user to select at least one diagnostic finding from the focused set of knowledge representation or by entering free-form text;

automatically generating a diagnostic report based on the selections or free-form text entries, and including the natural language statements describing the location in the anatomy of the region of interest; and retrievably storing the diagnostic report in an electronic medical record;

wherein a quality tracking routine uses analytics to review the free-form text entered by the user to study patterns and updates the knowledge representation.

24. An image reporting method, comprising the steps of:

retrieving an image representation of a sample structure from an image source;

automatically selecting a generic structure among a plurality of generic structures based on a comparison of content and imaging modality of the sample structure to content and imaging modality of the generic structure, the selected generic structure having coordinate data defined, the selected generic structure being related to the sample structure by both imaging modality and one or more attributes selected from the group of (size, dimensions, area, shape, volume, weight, density, location, anatomical organ, and orientation), at least one knowledge representation associated with said generic structure, the at least one knowledge representation being specific to the anatomical organ of the generic structure and an imaging modality used to capture the generic structure;

mapping the selected generic structure to the sample structure;

automatically determining at least one region of interest within the sample structure or prompting the user to select a region of interest;

linking the at least one region of interest with the coordinate data, thereby providing a spatial location of the at least one region of interest with respect to the sample structure;

for each said at least one region of interest providing a focused set of representations of diagnostic knowledge corresponding to the imaging modality and the at least one region of interest and prompting the user to select at least one diagnostic finding from the focused set of knowledge representation or enter free-form text; and automatically generating a diagnostic report based on the selections, spatial location of the at least one region of interest, and free-form text;

wherein a quality tracking routine retrieves one or more diagnostic reports for the at least one region of interest which were previously generated, compares the results of the each of the one or more diagnostic reports to identify a pattern of mischaracterizations, and adjusts the knowledge representation.

25. An image reporting method, comprising the steps of:

retrieving an image representation of a sample structure from an image source;

automatically selecting a generic structure among a plurality of generic structures based on a comparison of content and imaging modality of the sample structure to content and imaging modality of the generic structure, the plurality of generic structures having coordinate data defined therein, the selected generic structure being related to the sample structure by both imaging modality and one or more attributes selected from the group (size, dimensions, area, shape, volume, weight, density, location, anatomical organ, and orientation), at least one knowledge representation specific to an imaging modality used to capture the sample structure and the anatomical organ of the sample structure being associated with said generic structure;

mapping the selected generic structure to the sample structure;

automatically determining at least one region of interest within the sample structure or prompting the user to select a region of interest;

automatically generating natural language statements describing a location in the anatomy of the at least one region of interest using the coordinate data;

for each position on the anatomical organ, automatically providing a focused set of representations of diagnostic knowledge, and prompting the user to select at least one diagnostic finding from the focused set of knowledge representation or enter free-form text; and automatically generating a diagnostic report based on the selections and free-form text, and including the natural language statements describing the location in the anatomy of the region of interest; and retrievably storing the diagnostic report on an electronic storage medium, wherein said free-form text entries are used to update the knowledge representation.

* * * * *